United States Patent
Mori et al.

(10) Patent No.: US 10,743,783 B2
(45) Date of Patent: Aug. 18, 2020

(54) PULSE WAVE ANALYSIS APPARATUS, PULSE WAVE ANALYSIS METHOD, AND NON-TRANSITORY COMPUTER-READABLE STORAGE MEDIUM

(71) Applicant: FUJITSU LIMITED, Kawasaki-shi, Kanagawa (JP)

(72) Inventors: Tatsuya Mori, Sagamihara (JP); Daisuke Uchida, Atsugi (JP); Kazuho Maeda, Kawasaki (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 67 days.

(21) Appl. No.: 15/978,403

(22) Filed: May 14, 2018

(65) Prior Publication Data

US 2018/0256046 A1    Sep. 13, 2018

Related U.S. Application Data

(63) Continuation of application No. PCT/JP2015/082807, filed on Nov. 20, 2015.

(51) Int. Cl.
*A61B 5/024*    (2006.01)
*A61B 5/00*    (2006.01)
(Continued)

(52) U.S. Cl.
CPC .......... *A61B 5/02416* (2013.01); *A61B 5/024* (2013.01); *A61B 5/02405* (2013.01);
(Continued)

(58) Field of Classification Search
CPC ............ A61B 5/02416; A61B 5/02405; A61B 5/7207; A61B 5/7278; A61B 5/7246;
(Continued)

(56) References Cited

U.S. PATENT DOCUMENTS 9,750,461 B1 *   9/2017   Telfort ................. A61B 5/7221
2013/0226007 A1   8/2013   Jeanne et al.
(Continued)

FOREIGN PATENT DOCUMENTS

JP    2000-107147    4/2000
JP    2006-247221    9/2006
(Continued)

OTHER PUBLICATIONS

Extended European Search Report dated Sep. 20, 2018 in corresponding European Patent Application No. 15908833.5.
(Continued)

*Primary Examiner* — Amandeep Saini

(74) *Attorney, Agent, or Firm* — Staas & Halsey LLP

(57) ABSTRACT

A pulse wave analysis apparatus including a memory, and a processor coupled to the memory and the processor configured to execute a process, the process including extracting, from each of a plurality of captured images of a subject, a plurality of image areas corresponding to each of a plurality of parts of the subject respectively, generating pieces of waveform data corresponding to the plurality of parts based on an image analysis for the plurality of image areas, each of the pieces of waveform data indicating a pulse wave of the subject, calculating a first matching degree between the pieces of waveform data, and determining whether a noise is included in the pieces of waveform data based on the first matching degree.

14 Claims, 15 Drawing Sheets

(51) Int. Cl.
  *G06K 9/00* (2006.01)
  *G06T 7/00* (2017.01)
  *A61B 5/046* (2006.01)

(52) U.S. Cl.
  CPC .......... *A61B 5/7203* (2013.01); *A61B 5/7207* (2013.01); *A61B 5/7246* (2013.01); *A61B 5/7278* (2013.01); *G06K 9/0055* (2013.01); *G06T 7/0016* (2013.01); *A61B 5/046* (2013.01); *A61B 2576/00* (2013.01); *G06T 2207/10016* (2013.01); *G06T 2207/10024* (2013.01); *G06T 2207/30104* (2013.01); *G06T 2207/30201* (2013.01)

(58) Field of Classification Search
  CPC ... A61B 2576/00; A61B 5/046; A61B 5/7203; A61B 5/024; G06K 9/0055; G06T 7/0016; G06T 2207/10016; G06T 2207/10024; G06T 2207/30104; G06T 2207/30201
  USPC .......................................................... 382/128
  See application file for complete search history.

(56) References Cited

U.S. PATENT DOCUMENTS

| 2014/0276114 A1 | 9/2014 | Maeda et al. |
| 2014/0303454 A1 | 10/2014 | Clifton et al. |
| 2015/0126875 A1 | 5/2015 | Poh |
| 2015/0173630 A1 | 8/2015 | Uchida et al. |
| 2015/0254852 A1* | 9/2015 | Yamato ................ A61B 6/5288 345/634 |
| 2016/0338603 A1 | 11/2016 | Nakata et al. |
| 2018/0256047 A1* | 9/2018 | Mori ....................... A61B 5/024 |

FOREIGN PATENT DOCUMENTS

| JP | 2006247221 A * | 9/2006 |
| JP | 2014-502187 | 1/2014 |
| JP | 2014-176584 | 9/2014 |
| JP | 2014176584 A * | 9/2014 |
| JP | 2014-184002 | 10/2014 |
| JP | 2014-198201 | 10/2014 |
| JP | 2014-200390 | 10/2014 |
| JP | 2014-527863 | 10/2014 |
| JP | 2015-198789 | 11/2015 |
| WO | WO 2014/024104 A1 | 2/2014 |
| WO | WO 2014/038077 A1 | 3/2014 |
| WO | WO 2015/121949 A1 | 8/2015 |
| WO | WO 2016/116307 A1 | 7/2016 |

OTHER PUBLICATIONS

International Search Report, PCT/ISA/210, dated Feb. 16, 2016, in corresponding International Patent Application No. PCT/JP2015/082807.

International Written Opinion, PCT/ISA/237, dated Feb. 16, 2016, in corresponding International Patent Application No. PCT/JP2015/082807.

Japanese Office Action dated Mar. 19, 2019, in corresponding Japanese Patent Application No. 2017-551515.

* cited by examiner

PULSE WAVE ANALYSIS APPARATUS, PULSE WAVE ANALYSIS METHOD, AND NON-TRANSITORY COMPUTER-READABLE STORAGE MEDIUM

CROSS-REFERENCE TO RELATED APPLICATION

This application is a continuation application of International Application PCT/JP2015/082807 filed on Nov. 20, 2015 and designated the U.S., the entire contents of which are incorporated herein by reference.

FIELD

The present disclosure relates to a pulse wave analysis apparatus, a pulse wave analysis method, and a non-transitory computer-readable storage medium.

BACKGROUND

In the related art, there is a technology of measuring a pulse wave waveform of a subject by detecting a change in volume of blood that flows through a blood vessel of the subject based on a moving image obtained by photographing the subject. As a related art, for example, there is a technology of determining body movement of a person to be measured based on a characteristic value of a distribution waveform illustrating distribution of a light receiving level of a light receiving element in one direction by nipping a plurality of light receiving elements which receive transmitted light that is incident on the inside of the finger from a light generating element and has passed the finger with the finger. In addition, for example, there is a technology of processing data acquired from an input signal having physiological information that at least partially represents a periodic vital signal. In addition, for example, there is also a method of remotely monitoring vital signs by detecting a luminance signal in an image of a subject photographed by a video camera, such as a web camera.

CITATION LIST

Patent Literature

PTL 1: Japanese Laid-open Patent Publication No. 2000-107147
PTL 2: Japanese Laid-open Patent Publication No. 2014-502187
PTL 3: Japanese Laid-open Patent Publication No. 2014-527863

SUMMARY

According to one aspect of the present disclosure, a pulse wave analysis apparatus including a memory, and a processor coupled to the memory and the processor configured to execute a process, the process including extracting, from each of a plurality of captured images of a subject, a plurality of image areas corresponding to each of a plurality of parts of the subject respectively, generating pieces of waveform data corresponding to the plurality of parts based on an image analysis for the plurality of image areas, each of the pieces of waveform data indicating a pulse wave of the subject, calculating a first matching degree between the pieces of waveform data, and determining whether a noise is included in the pieces of waveform data based on the first matching degree.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

However, in the above-described related art, there is a case where it is not possible to analyze the pulse wave waveform of the subject with high accuracy. For example, in a case where the pulse wave waveform of the subject is disturbed, it is difficult to determine whether the pulse wave waveform is disturbed by noise caused by the body movement or the like of the subject, or the pulse wave waveform is disturbed by an arrhythmia or the like of the subject.

In one aspect, an object of the present disclosure is to provide a pulse wave analyzing apparatus, a pulse wave analyzing method, and a pulse wave analyzing program which can improve analysis accuracy of a pulse wave waveform of a subject.

Hereinafter, embodiments of a pulse wave analyzing apparatus, a pulse wave analyzing method, and a pulse wave analyzing program according to the present embodiment will be described in detail with reference to the drawings.

(One Example of Pulse Wave Analyzing Method According to Embodiment)

Figure 1:
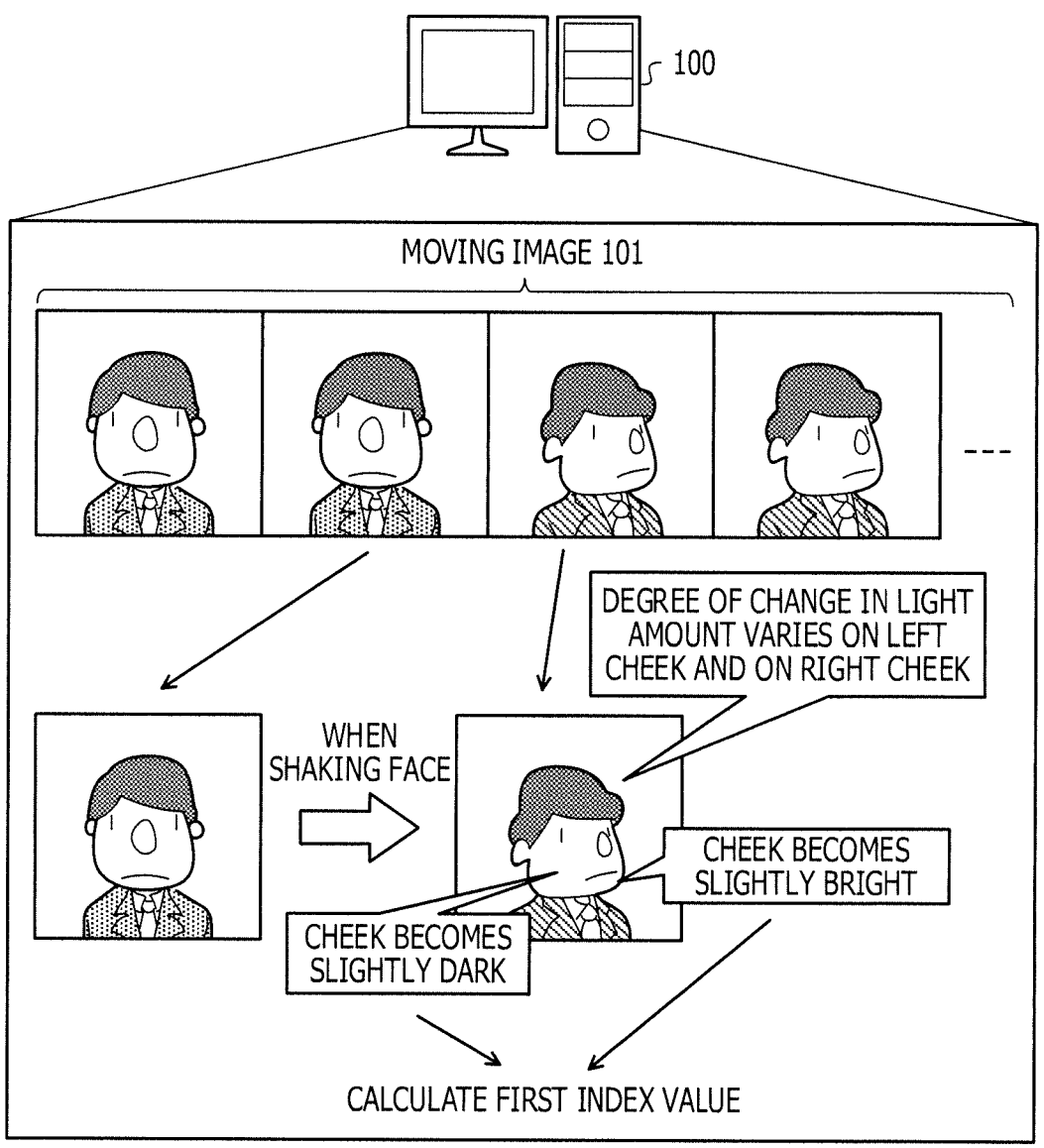
FIG. 1 is an explanatory view illustrating an example of a pulse wave analyzing method according to an embodiment.

FIG. 1 is an explanatory view illustrating an example of a pulse wave analyzing method according to an embodiment. In FIG. 1, a pulse wave analyzing apparatus 100 is a computer that supports analysis of a pulse wave waveform of a subject. The subject is the object to measure the pulse wave waveform. The subject is, for example, a human being. The pulse wave waveform is a waveform representing a temporal change in volume or pressure of blood that flows through a blood vessel of the subject with the beat of the heart.

Meanwhile, there has been a request to efficiently make determination concerning the health of the subject using biological information of the subject due to aging or an increase in medical expenses. For example, various types of information obtained from pulse wave waveforms in biological information of the subject are one of important indicators for viewing the life reaction of the subject, and are used for determining the health of the subject.

Specifically, the pulse rate can be an index representing the health condition of the subject. In addition, in a case where a state where the pulse rate is abnormally high (so-called tachycardia) is generated or lasts frequently despite the absence of a psychological stress load, there is no doubt that the function of the heart normally works. In addition, the fluctuation of the pulse wave interval for each beat can be an index representing the stress applied to the subject. Further, the pulse wave waveform can be an index indicating the blood vessel age of the subject. Further, the pulse wave waveform can be an index indicating whether or not the subject is in a state of arrhythmia leading to serious diseases, such as heart failure or cerebral infarction. Arrhythmia is that the rhythm of heart rate and pulse is not regular. In the arrhythmia state, the pulse wave waveform becomes a waveform that is not periodic.

In this manner, much information on the health condition of the subject can be obtained from the pulse wave waveform. Therefore, it is desirable to measure the pulse wave waveform of the subject efficiently, on a day-to-day basis continuously and without consciousness of the subject by the simplest possible method. For example, it is desirable to measure the pulse wave waveform of the subject noninvasively and noncontactly, even when the subject does not operate any device. Here, for example, a technology for noninvasively and noncontactly measuring the pulse wave waveform of the subject that corresponds to the volume change of the blood that flows through the blood vessel by utilizing the fact that the amount of light absorbed by the blood vessel of the subject depends on the blood flow rate and by analyzing the luminance change of the body surface of the subject from the moving image of the subject, is considered.

Meanwhile, there is a case where noise is included in the measured pulse wave waveform. For example, in a case where there is body movement of the subject, a moving image obtained by photographing the subject tends to include a component of noise caused by the body movement of the subject in addition to the component that corresponds to the signal of the pulse wave waveform. Therefore, for example, by keeping the subject static, there is a case where the component of noise included in the pulse wave waveform of the subject is reduced and the measurement accuracy of the pulse wave waveform of the subject is improved.

However, in this case, since it takes a burden to keep the subject static for a long time, it is difficult to measure the pulse wave waveform of the subject without routine and continuous consciousness of the subject. Furthermore, when the subject may not keep static, the noise that appears in the pulse wave waveform becomes large due to the body movement and the like of the subject, and it is not possible to avoid the inclusion of noise in the pulse wave waveform. As a result, since the pulse wave waveform contains noise, there is a case where it is not possible to analyze the pulse wave waveform with high accuracy. For example, in a case where disturbance occurs in the pulse wave waveform due to noise, there is a case where it is erroneously determined that the pulse wave waveform is disturbed due to the arrhythmia or the like of the subject. The disturbance of the pulse wave waveform means that the pulse wave waveform becomes a waveform which is not periodic.

Here, in the present embodiment, a pulse wave analyzing method by which it is possible to improve the analyzing accuracy of the pulse wave waveform of the subject by calculating an index value indicating likelihood of pulse waves of the pulse wave waveform of the subject from the moving image of the subject, even when the subject is not kept static, will be described.

The index value is a value indicating whether or not the pulse wave waveform is disturbed by noise caused by the body movement or the like of the subject in a case where the pulse wave waveform of the subject is disturbed. The index value indicates the degree of influence of the body movement of the subject on the pulse wave waveform. For example, the index value is a value that indicates a matching degree between the pulse wave waveforms of the pulse wave waveforms of each of the parts obtained by detecting a change in volume of the blood that flows through the blood vessel at each of the parts of the subject. Each of the parts is, for example, a left cheek and a right cheek of the subject. The body movement of the subject is, for example, shaking of the head of the subject. The pulse wave waveform of the part is a waveform similar to a pulse wave generated based on the luminance change of the part surface.

Here, the value indicating the matching degree between the pulse wave waveforms indicates a state where the body movement of the subject becomes large as the value becomes small and the pulse wave waveform is easily disturbed by the noise caused by the body movement of the subject, and indicates that the likelihood of pulse waves is small. Specifically, in a case where the body movement of the subject is relatively large, the degree of change in light amount that corresponds to each of the parts varies, and the degree of change in color of each of the parts varies, and thus, the degree of change in pulse wave waveforms of each of the parts also varies, and the value indicating the matching degree becomes smaller. Meanwhile, in a case where the body movement of the subject is relatively small, since the difference in degree of change in color of each of the parts is relatively small, the value indicating the matching degree becomes large.

In the example of FIG. 1, the pulse wave analyzing apparatus 100 extracts images of each part of the plurality of parts of the subject from each of the photographed images of the plurality of photographed images obtained by photographing the subject. The parts are a part of the body of the subject. The plurality of parts are, for example, a face, a left cheek and a right cheek.

The photographed image is data obtained by converting an optical signal from the subject at a certain point of time into an electric signal by a photoelectric conversion element.

The photographed image is data expressed by the size of each color of RGB with respect to the color of the subject by, for example, a Red, Green, and Blue (RGB) color model.

The plurality of photographed images are a plurality of images arranged in chronological order in the order of photographing. The plurality of photographed images are, for example, a series of photographed images included in a moving image 101. The moving image 101 is a series of frame images along the time series. The moving image 101 is, for example, a series of frame images photographed by the pulse wave analyzing apparatus 100. Further, the moving image 101 may be photographed by another computer. The moving image 101 may have already been photographed or may be being acquired in real time.

The pulse wave analyzing apparatus 100 acquires the moving image 101 obtained by photographing the face of the subject, for example. In addition, the pulse wave analyzing apparatus 100 extracts images of each of the parts of the plurality of parts of the subject from each of the photographed images included in the acquired moving image 101. The pulse wave analyzing apparatus 100 extracts the image of the left cheek of the subject and the image of the right cheek of the subject by using, for example, a technology of image recognition. The details of extracting the images of each of the parts will be described later with reference to FIGS. 4 to 6, for example.

The pulse wave analyzing apparatus 100 generates the pulse wave waveform of each of the parts by analyzing the images of each of the parts extracted from each of the photographed images. The pulse wave analyzing apparatus 100 analyzes the change in color of the left cheek of the subject based on the extracted image of the left cheek of the subject, detects the change in volume of blood that flows through the blood vessel on the left cheek of the subject, and generates a pulse wave waveform on the left cheek of the subject.

The pulse wave analyzing apparatus 100 analyzes the change in color of the right cheek of the subject based on the extracted image of the right cheek of the subject, detects the change in volume of blood that flows through the blood vessel on the right cheek of the subject, and generates a pulse wave waveform on the right cheek of the subject. The details of generating the pulse wave waveforms of each of the parts will be described later with reference to FIGS. 7 and 8, for example.

The pulse wave analyzing apparatus 100 calculates the first matching degree indicating a matching degree between the pulse wave waveforms of the generated pulse wave waveforms of each of the parts. The pulse wave analyzing apparatus 100 calculates the first matching degree indicating a matching degree between the pulse wave waveforms of the pulse wave waveforms of each of the parts, by using, for example, a correlation coefficient. The details of calculating the first matching degree between the pulse wave waveforms will be described later with reference to FIGS. 10, 11 and 12, for example.

The pulse wave analyzing apparatus 100 outputs the calculated first matching degree. For example, the pulse wave analyzing apparatus 100 correlates the calculated first matching degree with the pulse wave waveforms of each of the parts, displays the result on the display of the pulse wave analyzing apparatus 100, and notifies the user of the pulse wave analyzing apparatus 100 of the result. According to this, the pulse wave analyzing apparatus 100 can calculate the index value indicating the likelihood of the pulse wave waveform of subject based on the moving image 101 obtained by photographing the subject.

Accordingly, the pulse wave analyzing apparatus 100 can improve the analysis accuracy of the pulse wave waveform of the subject by calculating an index value indicating likelihood of pulse waves of the pulse wave waveform of the subject from the moving image 101 of the subject. For example, in a case where the calculated first matching degree is relatively small, the pulse wave analyzing apparatus 100 can determine that the noise is included in the generated pulse wave waveforms of each of the parts. The fact that the noise is included in the pulse wave waveform means that the noise included in the pulse wave waveform is large enough to be negligible in the analysis of the pulse wave waveform.

In addition, in a case where the noise included in the pulse wave waveform is small enough to be negligible in the analysis of the pulse wave waveform, the pulse wave analyzing apparatus 100 determines that the noise is not included. In addition, the pulse wave analyzing apparatus 100 can exclude the pulse wave waveform determined to include the noise from being used for determining the health of the subject, and the pulse wave waveform determined not to include the noise from being used for determining the health of the subject.

Here, a case where the pulse wave analyzing apparatus 100 photographs the subject and acquires the moving image 101 obtained by photographing the subject has been described, but the present embodiment is not limited thereto. For example, the pulse wave analyzing apparatus 100 may receive the moving image 101 photographed by another computer from another computer. Specifically, the pulse wave analyzing apparatus 100 may operate as a server, acquire the moving image 101 from a client apparatus, calculate an index value, and transmit the calculated index value, the determined result, or the like to the client apparatus.

(Example of Hardware Configuration of Pulse Wave Analyzing Apparatus 100)

Next, an example of the hardware configuration of the pulse wave analyzing apparatus 100 illustrated in FIG. 1 will be described with reference to FIG. 2. The pulse wave analyzing apparatus 100 is, for example, a server, a personal computer (PC), a note PC, a tablet PC, or a smartphone.

Figure 2:
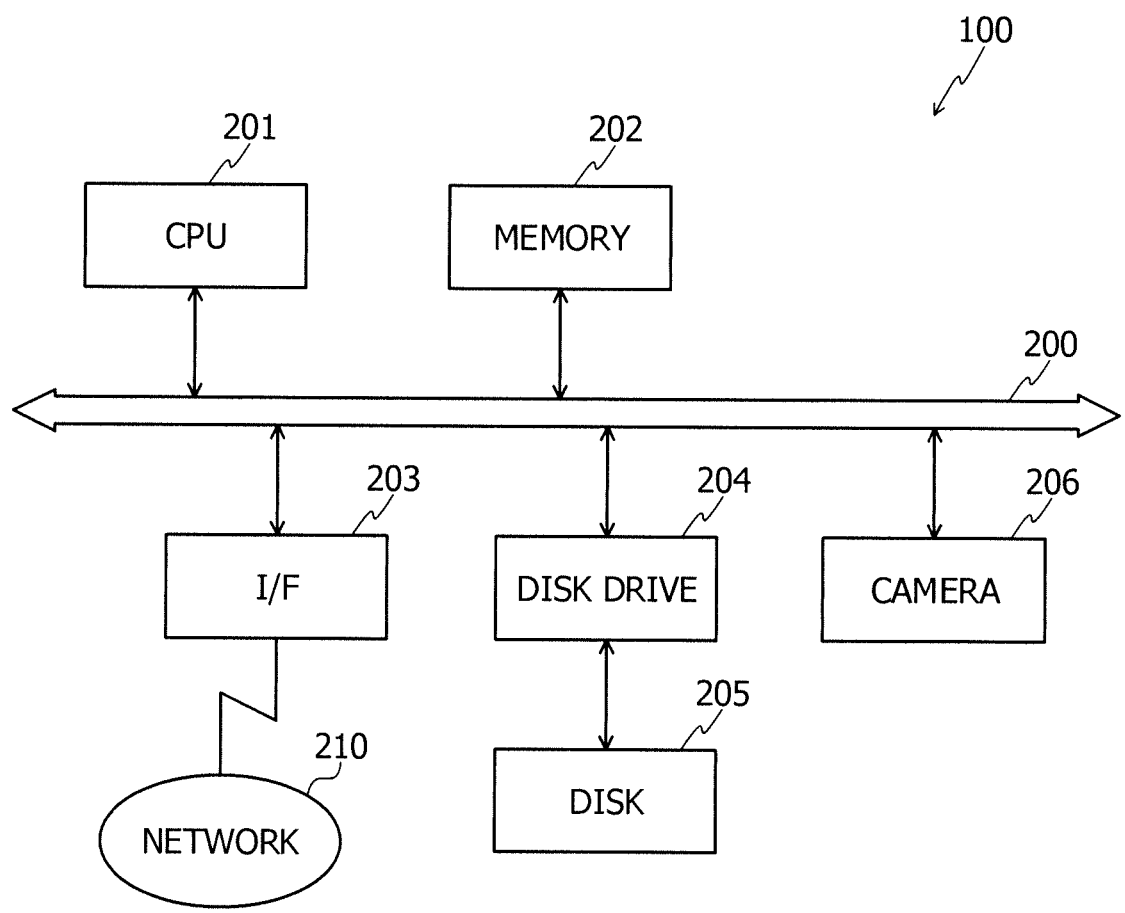
FIG. 2 is a view illustrating an example of a hardware configuration of a pulse wave analyzing apparatus 100.

FIG. 2 is a view illustrating an example of a hardware configuration of the pulse wave analyzing apparatus 100. In FIG. 2, the pulse wave analyzing apparatus 100 includes a central processing unit (CPU) 201, a memory 202, an interface (I/F) 203, a disk drive 204, a disk 205, and a camera 206. In addition, each of the components is connected to each other by a bus 200.

Here, the CPU 201 controls the entire pulse wave analyzing apparatus 100. The memory 202 includes, for example, a read only memory (ROM), a random access memory (RAM), and a flash ROM. Specifically, for example, the flash ROM or the ROM stores various programs, and the RAM is used as a work area of the CPU 201. The program stored in the memory 202 is loaded into the CPU 201, thereby causing the CPU 201 to execute the coded processing.

The I/F 203 is connected to a network 210 via a communication line, and is connected to another computer via the network 210. In addition, the I/F 203 controls the interface between the network 210 and the inside, and controls input and output of data from other computers. As the I/F 203, for example, a modem or a local area network (LAN) adapter can be adopted.

The disk drive 204 controls reading and writing of data from and to the disk 205 under the control of the CPU 201.

The disk drive 204 is, for example, a magnetic disk drive. The disk 205 is a nonvolatile memory that stores data written under the control of the disk drive 204.

The camera 206 is a device having a photoelectric conversion element, such as a charge coupled device (CCD) or a complementary metal oxide semiconductor (CMOS). The camera 206 converts the optical signal from the subject within the photographing range into an electric signal by the photoelectric conversion element, generates image data from the converted electric signal, and stores the generated image data in the memory 202 or the disk 205.

In addition to the above-described components, the pulse wave analyzing apparatus 100 may have, for example, a solid state drive (SSD), a semiconductor memory, a keyboard, a mouse, and a display. Further, instead of the disk drive 204 and the disk 205, the pulse wave analyzing apparatus 100 may have an SSD, a semiconductor memory, and the like.

(Example of Functional Configuration of Pulse Wave Analyzing Apparatus 100)

Figure 3:
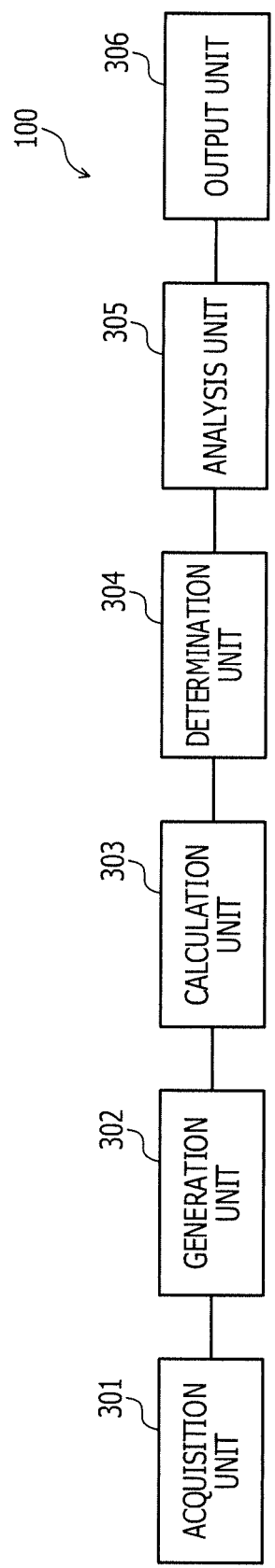
FIG. 3 is a block diagram illustrating an example of a functional configuration of the pulse wave analyzing apparatus 100.

Next, an example of the functional configuration of the pulse wave analyzing apparatus 100 will be described with reference to FIG. 3. FIG. 3 is a block diagram illustrating an example of a functional configuration of the pulse wave analyzing apparatus 100. The pulse wave analyzing apparatus 100 includes an acquiring unit 301, a generation unit 302, a calculation unit 303, a determination unit 304, an analysis unit 305, and an output unit 306.

The acquiring unit 301 to the output unit 306 function as a control unit, and for example, by causing the CPU 201 to execute a program stored in a storage area, such as the memory 202 or the disk 205 illustrated in FIG. 2, or by using the I/F 203, the function thereof is realized. The processing result of each of the functional units is stored in a storage area, such as the memory 202 and the disk 205.

The acquiring unit 301 acquires a plurality of photographed images obtained by photographing the subject. The subject is the object to measure the pulse wave waveform. The subject is, for example, a human being. The subject may be an animal. The plurality of photographed images are a plurality of images arranged in chronological order in the order of photographing. The plurality of photographed images are, for example, a plurality of images obtained by extracting the images from the moving image 101.

The plurality of photographed images are, for example, a series of photographed images included in a moving image 101. The plurality of photographed images may be a plurality of extracted frame images obtained by extracting the partial frame image satisfying a predetermined condition from the moving image 101. Specifically, the plurality of photographed images may be a plurality of frame images photographed at intervals of ⅙ seconds extracted from the moving image 101 photographed at intervals of 1/60 seconds.

In addition, the plurality of photographed images may be, for example, a series of processed frame images included in the moving image 101. Specifically, the plurality of photographed images may be a series of images represented by predetermined wavelength components obtained by extracting a predetermined wavelength component from a series of frame images included in the moving image 101. The plurality of photographed images may be a plurality of images successively photographed by a photographing apparatus, such as a digital camera capable of photographing a still image.

The acquiring unit 301 acquires the moving image 101 obtained by photographing the subject. The moving image 101 is, for example, a series of frame images photographed by using the photographing apparatus, such as a video camera capable of photographing a video. The moving image 101 obtained by photographing the subject is an image obtained by photographing at least a part of the body of the subject including the plurality of parts of the subject. A part of the body of the subject may be one of the plurality of parts of the subject. A part of the body of the subject is, for example, a face of the subject.

The plurality of parts include, for example, two or more interlocking parts. Two or more interlocking parts are parts that move similarly according to the movement of the subject. Two or more interlocking parts are, for example, the left cheek and nose of the subject who moves similarly in accordance with the movement of the face of the subject. In addition, the plurality of parts may include two or more parts which are not on the same plane. Two or more parts which are not on the same plane are, for example, two or more parts on a curved surface. Two or more parts not on the same plane are, for example, the left cheek and forehead of the subject.

In addition, the plurality of parts may include parts symmetrically existing in the body of the subject. Symmetrically existing parts are, for example, the left cheek and the right cheek symmetrically existing on the face of the subject. Two or more parts of the plurality of parts may be inclusive. The plurality of parts may include, for example, the face of the subject and the left cheek of the subject included in the face of the subject. Specifically, the plurality of parts may include the face of the subject, the left cheek of the face of the subject, and the right cheek of the face of the subject.

At least one of the plurality of parts is used as a part at which the pulse wave waveform to be determined whether or not the noise is included is generated. In addition, at least one of the plurality of parts is used as a part at which the pulse wave waveform of the calculation source of the index value is generated. The part at which the pulse wave waveform to be determined is generated and the part at which the pulse wave waveform of the calculation source of the index value is generated may overlap each other.

In addition, the plurality of parts of the subject may be a group of parts included in each of two or more different parts of the subject. Specifically, the acquiring unit 301 acquires the moving image 101 obtained by photographing the face of the subject by using the camera 206. Accordingly, the acquiring unit 301 can acquire the moving image of the subject who is the generation source of the pulse wave waveform of the subject.

The generation unit 302 extracts the images of each of the parts of the subject from each of the photographed images included in the moving image 101 acquired by the acquiring unit 301. The images of each of the parts of the subject are partial images in which at least a part of the body of the subject is taken in the photographed image. The image of the partial image may not have a fixed size in each of the photographed images. Each of the photographed images may be photographed images in which the partial image in which the body of subject is taken becomes equal to or greater than a predetermined size in the moving image 101.

In addition, the generation unit 302 generates the pulse wave waveforms of each of the parts by analyzing the images of each of the parts of the subject extracted from each of the photographed images. The analysis means, for example, detecting a change in volume of blood that flows through the blood vessel of the part based on the change in skin color at the part by performing spectral analysis on a series of images of each of the parts of the subject. The pulse wave waveform is a waveform which is obtained from the change in volume of blood that flows through the blood vessel of the subject, and represents a temporal change in volume of blood that flows through the blood vessel of the subject with the beat of the heart.

For example, the generation unit 302 extracts the partial image in which the face of the subject is taken in each of the photographed images, as the image in which a part at which the pulse wave waveform to be determined is generated is taken, from the moving image 101 acquired by the acquiring unit 301. The image of the partial image may not have a fixed size in each of the photographed images. In addition, the generation unit 302 analyzes the change in color of the face of the subject based on the extracted partial image in which the face of the subject is taken, and generates the pulse wave waveform for the blood vessels of the face of the subject by detecting the change in volume of the blood that flows through the blood vessel of the face of the subject. The generation unit 302 may further divide the generated pulse wave waveform of the face of the subject into partial waveforms for each predetermined period. The predetermined period is, for example, a period having a length that is a multiple of the estimated pulse period. Accordingly, the generation unit 302 can generate the pulse wave waveform of the subject who is a subject of determining whether or not the noise is included.

For example, the generation unit 302 extracts the partial image in which the left cheek of the face of the subject is taken in each of the photographed images and the partial image in which the right cheek of the subject is taken, as the image in which a part at which the pulse wave waveform of the calculation source of the index value is generated is taken, from the moving image 101 acquired by the acquiring unit 301. In addition, the generation unit 302 analyzes the change in color of the left cheek of the subject based on the extracted partial image in which the left cheek of the subject is taken, and generates the pulse wave waveform for the blood vessels of the left cheek of the subject by detecting the change in volume of the blood that flows through the blood vessel of the left cheek of the subject. The generation unit 302 may further divide the generated pulse wave waveform of the left cheek of the subject into partial waveforms for each predetermined period.

In addition, the generation unit 302 analyzes the change in color of the right cheek of the subject based on the extracted partial image in which the right cheek of the subject is taken, and generates the pulse wave waveform for the blood vessels of the right cheek of the subject by detecting the change in volume of the blood that flows through the blood vessel of the right cheek of the subject. The generation unit 302 may further divide the generated pulse wave waveform of the right cheek of the subject into partial waveforms for each predetermined period. Accordingly, the generation unit 302 can generate the pulse wave waveforms of each of the parts used when determining whether or not the noise is included. Accordingly, specifically, the generation unit 302 can generate the pulse wave waveforms of each of the parts used when the calculation unit 303 calculates the index value indicating likelihood of pulse wave.

Here, for example, the pulse wave waveform that serves as a subject to be determined whether or not the noise is included and the pulse wave waveform used when calculating the index value may be at least the same pulse wave waveform generated from the plurality of photographed images, may be different pulse wave waveforms, or may overlap each other.

The calculation unit 303 calculates the index value indicating the likelihood of pulse waves of the pulse wave waveforms generated by the generation unit 302. The first index value is a value indicating whether or not the pulse wave waveform is disturbed by noise caused by the body movement or the like of the subject in a case where the pulse wave waveform of the subject is disturbed. The index value is, for example, a first matching degree indicating a matching degree between at least one of the pulse wave waveforms of the pulse wave waveforms of each of the parts of the subject. The index value may be a statistical value, such as an average value, a median value, a maximum value, and a minimum value of the first matching degree indicating the matching degree between the pulse wave waveforms of the pulse wave waveforms of each of the parts of the subject.

Further, the index value may be, for example, a second matching degree indicating a matching degree between different partial waveforms in the pulse wave waveforms at any part. The second matching degree is a value that indicates how periodically the pulse wave waveform of the subject is periodic (degree of periodicity) and indicates how similar partial waveforms appear repeatedly in the pulse wave waveform of the subject. In addition, the second matching degree indicates how disturbed the pulse wave waveform of the subject is.

Here, the second matching degree indicating the matching degree between the partial waveforms indicates that the disturbance of the pulse wave waveforms at any part of the subject becomes large as the value becomes small. Specifically, according to the body movement or the arrhythmia of the subject, the amplitude of the pulse wave waveform at any part of the subject changes, partial waveforms similar to each other in the pulse wave waveform at any part are not repeated, and the value indicating the matching degree between the partial waveforms becomes small. Meanwhile, when there is no body movement or arrhythmia of the subject, the pulse wave waveform at any part becomes a periodic waveform that corresponds to the contraction or expansion of the heart, partial waveforms similar to each other in the pulse wave waveform at any part are repeated, and the value indicating the matching degree between the partial waveforms become large.

In addition, the second matching degree may be a value indicating the magnitude of the variation in the pulse wave interval of the pulse wave waveforms at any part of the subject. The second matching degree may be, for example, a standard deviation of a difference between maximum values or minimum values adjacent to each other in the pulse wave waveforms at any part of the subject. In addition, the second matching degree may be, for example, the standard deviation of the pulse wave interval in the pulse wave waveform at any part of the subject. Further, the second matching degree may be, for example, a peak width of spectral distribution obtained from the pulse wave waveform at any part of the subject. Further, the second matching degree may be, for example, a peak ratio of spectral distribution obtained from the pulse wave waveform at any part of the subject. The peak ratio is, for example, a ratio between the maximum value and the second largest value in the spectral distribution.

The calculation unit 303 calculates the first matching degree indicating a matching degree between the pulse wave waveforms of the pulse wave waveforms of each of the parts generated by the generation unit 302, by using, for example, a correlation coefficient. Specifically, the calculation unit 303 calculates the first matching degree indicating a matching degree between the pulse wave waveform of the left cheek of the subject and pulse wave waveform of the right cheek of the subject, which is generated as the pulse wave waveform of the part at which the pulse wave waveform of the calculation subject of the index value is generated.

In addition, specifically, in a case where the plurality of parts include three or more parts, for each predetermined combination of the plurality of parts, the calculation unit 303 may calculate the first matching degree indicating the matching degree between the pulse wave waveforms of the pulse wave waveforms of each of the parts in the combination. Accordingly, the calculation unit 303 can calculate the first matching degree used as the index value indicating the likelihood of pulse waves.

Further, for example, the calculation unit 303 extracts a plurality of partial waveforms that corresponds to a predetermined time from the pulse wave waveforms at any part of the subject generated by the generation unit 302, and calculates the second matching degree indicating the matching degree between the partial waveforms of the plurality of extracted partial waveforms by using the correlation coefficient. Accordingly, the calculation unit 303 can calculate the second matching degree used as the index value indicating the likelihood of pulse waves.

The determination unit 304 determines whether or not the noise is included in the pulse wave waveform of the subject generated by the generation unit 302 based on the first matching degree calculated by the calculation unit 303. The noise is a disturbance of the pulse wave waveform caused by the body movement or the like of the subject. The determination unit 304 determines that the noise is included in the pulse wave waveform of the face of the subject generated by the generation unit 302, for example, in a case where the first matching degree calculated by the calculation unit 303 is equal to or less than the first threshold value. Accordingly, the determination unit 304 can distinguish a pulse wave waveform including relatively large noise and a pulse wave waveform including relatively small noise to the extent of being negligible when analyzing the pulse wave waveform.

Further, in a case where the plurality of parts include three or more parts, the determination unit 304 may determine whether or not the noise is included in the pulse wave waveform of the subject generated by the generation unit 302 based on the statistical value of the first matching degree between the pulse wave waveforms of the pulse wave waveforms at three or more parts, for example, an average value. The statistical values are, for example, an average value, a median value, a maximum value, and a minimum value. The determination unit 304 determines that the noise is included in the pulse wave waveform of the face of the subject generated by the generation unit 302, for example, in a case where the average value of the first matching degree is equal to or less than the first threshold value. Accordingly, the determination unit 304 can distinguish a pulse wave waveform including relatively large noise and a pulse wave waveform including relatively small noise to the extent of being negligible when analyzing the pulse wave waveform.

Further, in a case where the plurality of parts include three or more parts, the determination unit 304 determines whether or not the noise is included in the pulse wave waveform of the subject generated by the generation unit 302 based on the statistical value of the first matching degree for each combination, for example, the minimum value. The determination unit 304 determines that the noise is included in the pulse wave waveform of the face of the subject generated by the generation unit 302, for example, in a case where the minimum value of the first matching degree is equal to or less than the first threshold value. Accordingly, the determination unit 304 can distinguish a pulse wave waveform including relatively large noise and a pulse wave waveform including relatively small noise to the extent of being negligible when analyzing the pulse wave waveform.

In addition, the determination unit 304 may determine whether or not the noise is included in the pulse wave waveform of the subject generated by the generation unit 302 based on the second matching degree calculated by the calculation unit 303. The determination unit 304 determines that the noise is included in the pulse wave waveform of the face of the subject generated by the generation unit 302 in a case where the second matching degree calculated by the calculation unit 303 is equal to or less than the second threshold value. Accordingly, the determination unit 304 can distinguish a pulse wave waveform including relatively large noise and a pulse wave waveform including relatively small noise to the extent of being negligible when analyzing the pulse wave waveform.

In addition, the determination unit 304 may determine whether or not the noise is included in the pulse wave waveform of the subject generated by the generation unit 302 based on the first matching degree calculated by the calculation unit 303 and the second matching degree calculated by the calculation unit 303. The determination unit 304 determines that the noise is included in the pulse wave waveform of the face of the subject generated by the generation unit 302, for example, in a case where the first matching degree calculated by the calculation unit 303 is equal to or less than the first threshold value and the second matching degree calculated by the calculation unit 303 is equal to or less than the second threshold value. Accordingly, the determination unit 304 can distinguish a pulse wave waveform including relatively large noise and a pulse wave waveform including relatively small noise to the extent of being negligible when analyzing the pulse wave waveform.

In addition, the determination unit 304 may determine whether or not the noise is included in the pulse wave waveforms at any part of the plurality of parts based on the first matching degree calculated by the calculation unit 303. The determination unit 304 determines that the noise is included in the pulse wave waveform of the part, for example, in a case where all of the first matching degrees related to a certain part calculated by the calculation unit 303 are equal to or less than the first threshold value. Accordingly, the determination unit 304 can distinguish a pulse wave waveform including relatively large noise and a pulse wave waveform including relatively small noise to the extent of being negligible when analyzing the pulse wave waveform.

The analysis unit 305 analyzes the pulse wave waveform of the subject based on the result determined by the determination unit 304. For example, the analysis unit 305 calculates the pulse rate of the subject by using the pulse wave waveform determined to include no noise as a result of determination by the determination unit 304. Accordingly, the analysis unit 305 can analyze the pulse wave waveform of the subject and make a determination regarding the health of the subject.

The output unit 306 outputs at least one of the first matching degree calculated by the calculation unit 303, the second matching degree calculated by the calculation unit 303, the result determined by the determination unit 304, and the result analyzed by the analysis unit 305. The output format includes, for example, display on a display, printout to a printer, transmission to an external device by the I/F 203, storage in a storage region, such as the memory 202 or the disk 205, and the like.

The output unit 306 outputs, for example, the first matching degree calculated by the calculation unit 303 and the pulse wave waveform of the subject generated by the generation unit 302 in association with each other. Specifically, the output unit 306 outputs the first matching degree calculated by the calculation unit 303 and the pulse wave waveform of the face of the subject generated by the generation unit 302 in association with each other. Accordingly, the output unit 306 can notify the user of the calculated first matching degree as the index value of likelihood of pulse waves for the pulse wave waveform of the subject.

The output unit 306 outputs, for example, the first matching degree calculated by the calculation unit 303 and the pulse wave waveforms at any part of the plurality of parts generated by the generation unit 302 in association with each other. Specifically, the output unit 306 outputs the first matching degree calculated by the calculation unit 303 and the pulse wave waveform of the left cheek or the right cheek of the subject generated by the generation unit 302 in association with each other. Accordingly, the output unit 306 can notify the user of the calculated first matching degree as the index value of the likelihood of pulse waves for the pulse wave waveforms at any part of the plurality of parts.

The output unit 306 may further output the first matching degree calculated by the calculation unit 303 and the second matching degree calculated by the calculation unit 303 in association with each other.

The output unit 306 outputs, for example, the result determined by the determination unit 304 and the pulse wave waveform of the subject generated by the generation unit 302 in association with each other. Specifically, the output unit 306 outputs the result determined by the determination unit 304 and the pulse wave waveform of the face of the subject generated by the generation unit 302 in association with each other.

The output unit 306 outputs, for example, the result analyzed by the analysis unit 305 and the pulse wave waveform of the subject generated by the generation unit 302 in association with each other. Specifically, the output unit 306 outputs the result analyzed by the analysis unit 305 and the pulse wave waveform of the face of the subject generated by the generation unit 302 in association with each other.

(Example of Generating Pulse Wave Waveform of Subject and Determining Whether or not Noise is Included in Pulse Wave Waveform)

Next, with reference to FIGS. 4 to 13, an example will be described in which the pulse wave analyzing apparatus 100 generates the pulse wave waveform of the subject and determines whether or not the noise is included in the pulse wave waveform.

First, the pulse wave analyzing apparatus 100 acquires the moving image 101 obtained by photographing the subject. The moving image 101 is, for example, a series of photographed images expressed by the luminance of RGB. Further, the moving image 101 may be expressed by luminance of a color belonging to a wavelength band different from that of RGB. In addition, the moving image 101 may be expressed by near-infrared or red brightness.

Further, the moving image 101 may be, for example, a series of data correlated with luminance. As for the moving image 101, for example, similar to a series of data acquired by a laser speckle blood flow meter, when the signal intensity varies depending on how the light hits, the signal intensity may depend on the amount and the speed of red blood cells.

Next, the pulse wave analyzing apparatus 100 extracts a predetermined image of the subject from the acquired moving image 101. The predetermined image is, for example, an image of a part of the body of the subject including the plurality of parts of the subject. The part of the body of the subject may be one of the plurality of parts of the subject. The part of the body is, for example, a face, an arm, a neck, an ankle, a hand, and a finger. The plurality of parts are, for example, a face that is a part of the body, and a left side of the face, a right side of the face, a forehead, a left cheek, and a right cheek, which are further parts of the face that is a part of the body.

For example, similar to any of the first to third examples which will be described later with reference to FIGS. 4 to 6, the pulse wave analyzing apparatus 100 extracts the images of each of the parts of the subject who is the generation source of the pulse wave waveforms of each of the parts of the subject from the acquired moving image 101. Here, the description of FIG. 4 will be made.

<First Example of Extracting Images of Each of Parts of Subject>

Figure 4:
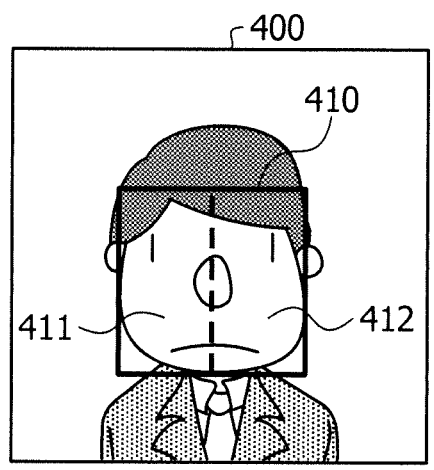
FIG. 4 is an explanatory view illustrating a first example of extracting images of each part of a subject.

FIG. 4 is an explanatory view illustrating a first example of extracting the images of each of the parts of the subject. Here, in the pulse wave analyzing apparatus 100, it becomes easy to measure the pulse wave waveform with high accuracy when the region where the body of the subject appears in the image of the generation source of the pulse wave waveform is large. Meanwhile, in the pulse wave analyzing apparatus 100, it becomes difficult to measure the pulse wave waveform with high accuracy when the region other than the body of the subject is included in the image of the generation source of the pulse wave waveform. For example, since a region, such as a background where no subject is photographed, exhibits luminance other than the part of the subject, it is possible to generate the noise to the pulse wave waveform of the part of the subject.

Therefore, it is preferable that the pulse wave analyzing apparatus 100 extracts an image of each of the parts of the subject such that the region where each of the parts of the subject appears becomes large and the region where the part other than each of the parts of the subject appears becomes small. Further, the pulse wave analyzing apparatus 100 may not necessarily extract the images of each of the parts of the subject from all of the photographed images in the moving image 101. For example, when the region where each of the parts of the subject appears in any one of the photographed images of the moving image 101 is equal to or less than a certain value, the pulse wave analyzing apparatus 100 may not extract the image of each of the parts of the subject from the photographed image.

In FIG. 4, for each of the photographed images 400 of the moving image 101, the pulse wave analyzing apparatus 100 detects the region where the face of the subject is taken by using the face detection engine, and extracts an image 410 of the face of the subject. The face detection engine is software for detecting a human face and a region of the human face where parts, such as a forehead, a nose, a mouth, eyes, or cheeks, from a predetermined image. The pulse wave analyzing apparatus 100 further divides the image 410 of the face of the subject extracted from each of the photographed images 400 of the moving image 101 into left and right images, and extracts an image 411 on the left side of the face and an image 412 on the right side of the face.

Next, the pulse wave analyzing apparatus 100 sets to use the image 410 of the face of the subject having a relatively large region where the body of the subject is taken, as the image of the generation source of the pulse wave waveform to be determined whether or not the noise is included and to be analyzed. In addition, the pulse wave analyzing apparatus 100 sets to use the image 410 of the face of the subject, the image 411 on the left side of the remaining face, and the image 412 on the right side of the face, as images of calculation source of the index value of likelihood of pulse wave.

At this time, the pulse wave analyzing apparatus 100 may not necessarily extract the image 410 of the face of the subject, the image 411 on the left side of the face, and the image 412 on the right side of the face from all of the photographed images 400 among the photographed images 400 included in the moving image 101. For example, the pulse wave analyzing apparatus 100 may not extract the image 411 on the left side of the face and the image 412 on the right side of the face from the photographed image 400 in which the image 411 on the left side of the face or the image 412 on the right side of the face is equal to or less than the predetermined size. Accordingly, the pulse wave analyzing apparatus 100 can reduce a processing amount and suppress an increase in processing time. Here, the description of FIG. 5 will be made.

<Second Example of Extracting Images of Each of Parts of Subject>

Figure 5:
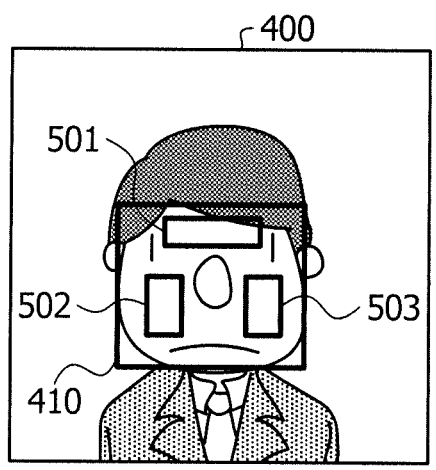
FIG. 5 is an explanatory view illustrating a second example of extracting images of each of the parts of the subject.

FIG. 5 is an explanatory view illustrating a second example of extracting the images of each of the parts of the subject. Here, by using the images of each of the parts of three or more parts of the subject as the image of the calculation source of the index value of the likelihood of the pulse wave, the pulse wave analyzing apparatus 100 may calculate the index value of the likelihood of the pulse wave in consideration of various body movements of the subject.

For example, the pulse wave analyzing apparatus 100 includes an image of a part existing in the lateral direction of the face of the subject as the image of the calculation source of the index value of the likelihood of the pulse wave, and includes the image of the part existing in the vertical direction of the face of the subject. The image of the part existing in the lateral direction of the face of the subject and the image of the part existing in the vertical direction of the face of the subject may include overlapping images. Accordingly, the pulse wave analyzing apparatus 100 can further consider the noise caused by the left and right movement of the face of the subject and the noise caused by the up and down movement of the face of the subject.

In FIG. 5, for each of the photographed images 400 of the moving image 101, the pulse wave analyzing apparatus 100 detects the region where the face of the subject is taken by using the face detection engine, and extracts an image 410 of the face of the subject. By using the face detection engine, the pulse wave analyzing apparatus 100 further detects a region where the forehead of the subject is taken, a region where the left cheek is taken, and a region where the right cheek is taken, and extracts an image 501 of the forehead of the subject, an image 502 of the left cheek, and an image 503 of the right cheek. Accordingly, the pulse wave analyzing apparatus 100 can calculate the index value of the likelihood of the pulse wave in consideration of the up and down movement of the face or the like other than the left and right movement of the face. Here, the description of FIG. 6 will be made.

<Third Example of Extracting Images of Each of Parts of Subject>

Figure 6:
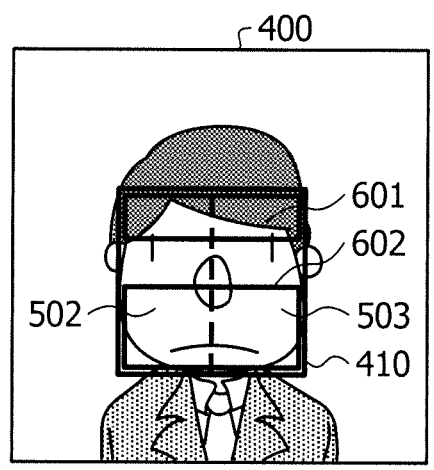
FIG. 6 is an explanatory view illustrating a third example of extracting images of each of the parts of the subject.

FIG. 6 is an explanatory view illustrating a third example of extracting the images of each of the parts of the subject. Here, in the body of the subject, a part at which it is difficult to keep a state where the subject is static and it is easy to generate the noise in the pulse wave waveform exists. For example, the eye of the subject may cause noise in the pulse wave waveform due to blinking.

Therefore, the pulse wave analyzing apparatus 100 may extract an image excluding a part at which it is difficult to keep a state where the subject is static, and which is likely to cause noise in the pulse wave waveform. Accordingly, the pulse wave analyzing apparatus 100 can easily calculate the index value of the likelihood of the pulse wave with high accuracy.

In FIG. 6, for each of the photographed images 400 of the moving image 101, the pulse wave analyzing apparatus 100 detects the region where the face of the subject is taken by using the face detection engine, and extracts an image 410 of the face of the subject. By using the face detection engine, the pulse wave analyzing apparatus 100 further detects the region where the eyes of the subject are taken and excludes the region where the eyes of the subject are taken from the region where the face of the subject is taken.

Further, the pulse wave analyzing apparatus 100 further extracts the image 601 of the upper part of the face above the region where the eyes of the subject are taken, in the image 410 of the face of the subject. Further, the pulse wave analyzing apparatus 100 further extracts the image 602 of the lower part of the face below the region where the eyes of the subject are taken, in the image 410 of the face of the subject. In addition, the pulse wave analyzing apparatus 100 further extracts the image 502 of the left cheek and the image 503 of the right cheek in the image 602 of the lower part of the face of subject. Accordingly, the pulse wave analyzing apparatus 100 can extract an image excluding a region where the noise of the eyes or the like is likely to be generated, and reduce the noise.

Hereinafter, similar to the first example illustrated in FIG. 4, the description of the example will continue using a case where the pulse wave analyzing apparatus 100 extracts the image 410 of the face of the subject, the image 411 on the left side of the face of the subject, and the image 412 on the right side of the face of the subject as an example.

Based on the extracted image 410 of the face of the subject, the image 411 on the left side of the face, and the image 412 on the right side of the face, the pulse wave analyzing apparatus 100 generates the pulse wave waveform of the face of the subject, the pulse wave waveform on the left side of the face, and the pulse wave waveform on the right side of the face. The pulse wave analyzing apparatus 100 generates the pulse wave waveform of the face of the subject, the pulse wave waveform on the left side of the face, and the pulse wave waveform on the right side of the face, for example, similar to one example which will be described in FIGS. 7 and 8 later. Here, the description of FIG. 7 will be made.

<One Example of Generating Pulse Wave Waveforms of Each of Parts of Subject>

Figure 7:
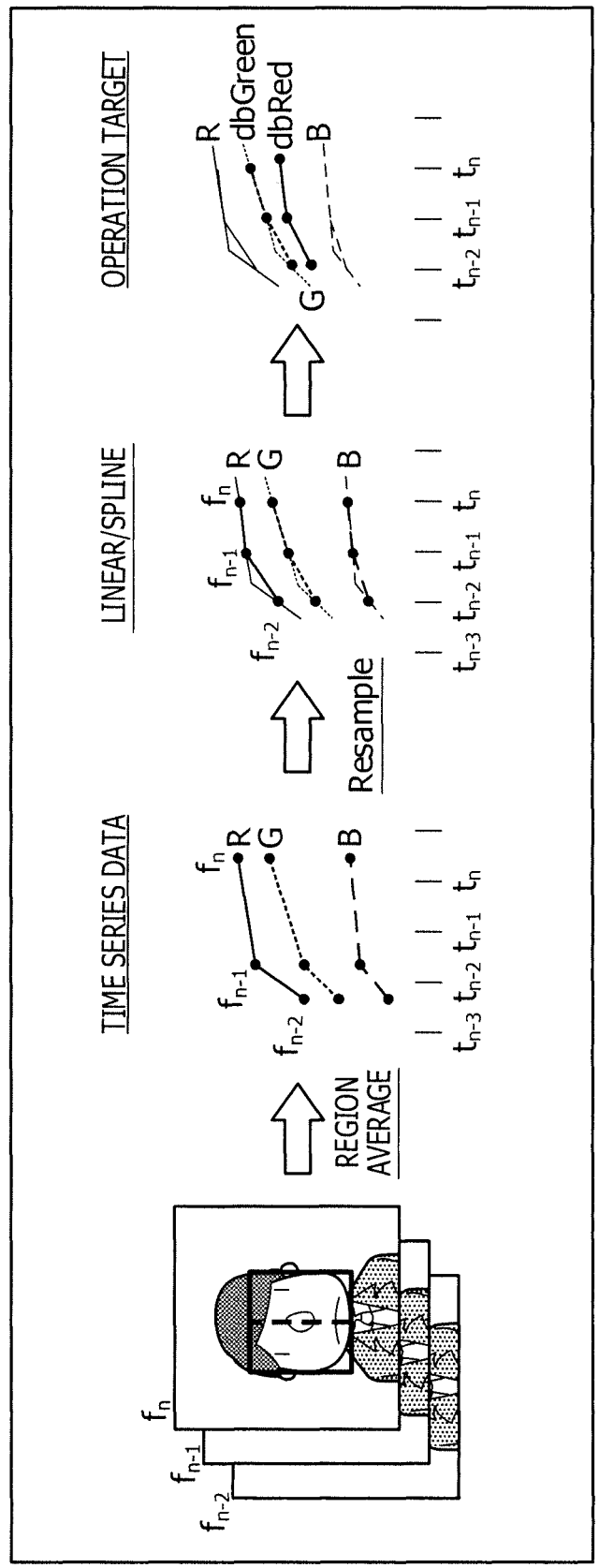
FIG. 7 is an explanatory view (part 1) illustrating an example of generating pulse wave waveforms of each of the parts of the subject.
Figure 8:
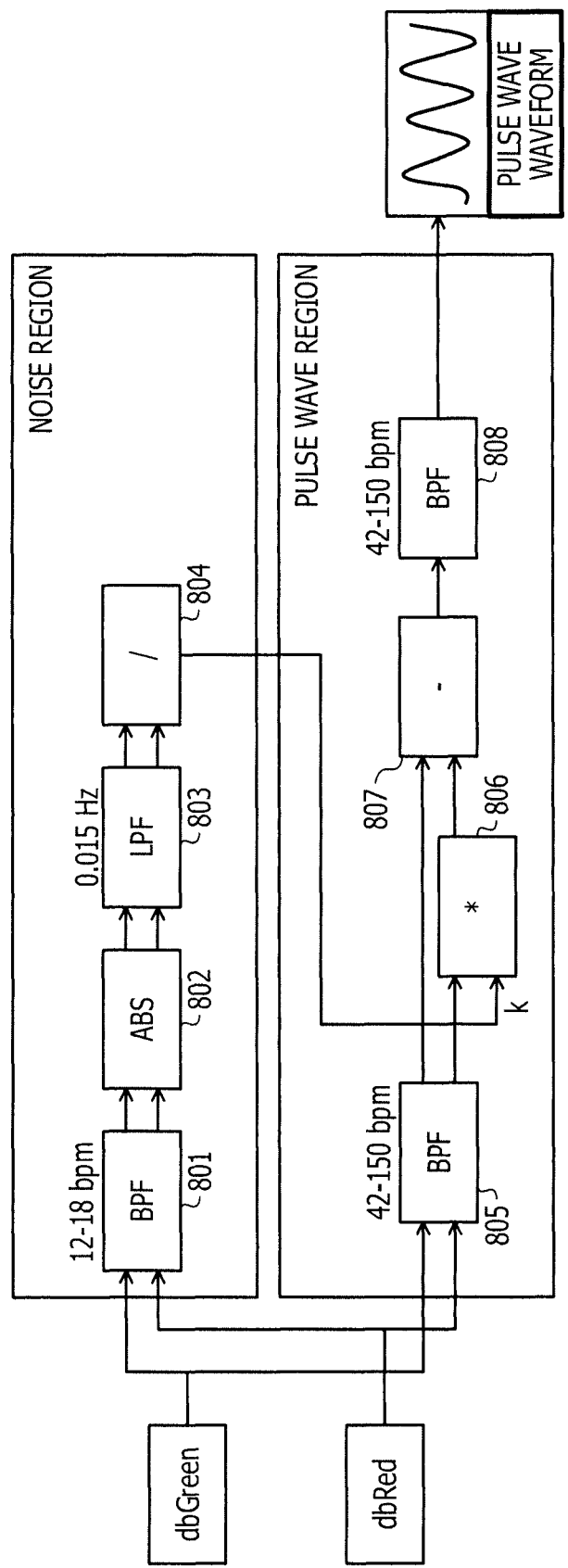
FIG. 8 is an explanatory view (part 2) illustrating an example of generating the pulse wave waveforms of each of the parts of the subject.

FIGS. 7 and 8 are explanatory views illustrating an example of generating the pulse wave waveforms of each of the parts of the subject. As a technology for generating the pulse wave waveform, for example, it is possible to refer to the technology described in International Publication Pamphlet No. WO 2014/038077.

Here, depending on the contraction or expansion of the heart, the flow rate of the blood that flows through the blood vessel of the human body varies. In addition, the amount of light absorbed by the blood vessel of the subject tends to depend on the flow rate of blood that flows through the blood vessel. Therefore, in accordance with the contraction or expansion of the heart, the luminance of the image of the part of the subject in the photographed image also changes, and the luminance that corresponds to the pulse at the part of the subject is obtained. In other words, the time series data of the representative value of the predetermined wavelength component in the image of the part of the subject in the photographed image becomes the time series data including the pulse component of the part of the subject.

Meanwhile, there is a case where the luminance of the image of the part of the subject in the photographed image changes in accordance with the change in light amount that corresponds to the part of the subject due to the body movement or the like of the subject. Therefore, there is a case where the time series data of the representative value of the predetermined wavelength component in the image of the part of the subject in the photographed image also includes a noise component different from the pulse component for the part of the subject. Here, the pulse wave analyzing apparatus 100 acquires the time series data of the representative values of the plurality of wavelength components, performs predetermined calculation using a filter or the like which will be described later, reduces the noise component from the time series data of the representative value of the predetermined wavelength component of the photographed image, and generate the pulse wave waveform of the part of the subject.

In FIG. 7, based on the images at any part of the subject extracted from each of the photographed images f(1), . . . , f(n), the pulse wave analyzing apparatus 100 acquires the time series data of the representative value of the predetermined wavelength component included in the image. For example, the pulse wave analyzing apparatus 100 acquires the time series data of the representative values of an R component, a G component, and a B component included in the image at any part of the subject. The representative values of the R component, the G component, and the B component are, for example, average values of the R component, the G component, and the B component, respectively.

In a case where the time series data of the acquired representative value is not the time series data of an equal time interval, the pulse wave analyzing apparatus 100 converts the time series data of the representative value into the time series data of the equal time interval by a resampling technology that uses linear approximation or spline approximation. The time series data at equal time intervals are time series data of the representative values of the predetermined wavelength components at each of the times t(1), . . . , t(n).

Since the hemoglobin in the blood has characteristics of absorbing green light, the pulse wave analyzing apparatus 100 sets the time series data of the representative value of the G component having a relatively high degree of representing the pulse component as dbGreen. In addition, the pulse wave analyzing apparatus 100 generates the time series data of the average value of the representative value of the R component and the representative value of the B component other than the representative value of the G component, and sets the time series data as dbRed. Here, the description of FIG. 8 will be made.

In FIG. 8, the pulse wave analyzing apparatus 100 extracts signal components in a specific frequency band of the dbRed by a band pass filter (BPF) 801. The specific frequency band is, for example, a frequency of 12 bpm or greater and less than 18 bpm. In addition, the pulse wave analyzing apparatus 100 extracts the signal component of the specific frequency band of the dbGreen by the BPF 801.

Next, the pulse wave analyzing apparatus 100 extracts the time series data of the absolute value of the signal component of the specific frequency band of the dbRed by an operation unit 802. In addition, the pulse wave analyzing apparatus 100 extracts the time series data of the absolute value of the signal component of the specific frequency band of the dbGreen by an operation unit 802.

In addition, the pulse wave analyzing apparatus 100 performs a smoothing process on the time series data of the absolute value of the specific frequency band of dbRed by a low pass filter (LPF) 803, and removes steep frequency components. In addition, the pulse wave analyzing apparatus 100 performs a smoothing process with respect to the time series data of the absolute value of the specific frequency band of the dbGreen by the LPF 803, and removes steep frequency components.

Next, the pulse wave analyzing apparatus 100 calculates the correction coefficient k by the operation unit 804 by dividing the absolute value of the specific frequency band of the smoothed dbRed by the absolute value of the specific frequency band of the smoothed dbGreen.

In addition, the pulse wave analyzing apparatus 100 extracts the signal component of the pulse wave frequency band of the dbRed by a BPF 805. The pulse wave frequency band is, for example, a frequency of 42 bpm or greater and less than 150 bpm. In addition, the pulse wave analyzing apparatus 100 extracts the signal component of the specific frequency band of the dbGreen by the BPF 805.

Next, in the pulse wave analyzing apparatus 100, an operation unit 806 multiplies the signal component in the pulse wave frequency band of the extracted dbRed by the calculated correction coefficient k. In addition, in the pulse wave analyzing apparatus 100, an operation unit 807 subtracts the signal component of the pulse wave frequency band of the dbRed multiplied by the correction coefficient k from the signal component of the pulse wave frequency band of the extracted dbGreen.

Next, the pulse wave analyzing apparatus 100 extracts the signal component of the pulse wave frequency band of the time series data of the signal after the subtraction by the BPF 808. In addition, the pulse wave analyzing apparatus 100 sets the extracted waveform as the pulse wave waveforms at any part of the subject.

Here, a case where the pulse wave analyzing apparatus 100 acquires the time series data of the representative values of the plurality of wavelength components has been described, but the present embodiment is not limited thereto. For example, the pulse wave analyzing apparatus 100 may extract the signal component in the pulse wave frequency band from the time series data of the representative value of the predetermined wavelength component by the BPF, and may set the extracted waveform as the pulse wave waveforms at any part of the subject.

Here, a case where the pulse wave analyzing apparatus 100 generates the pulse wave waveform based on the luminance that corresponds to the flow rate of the blood has been described, but the present embodiment is not limited thereto. For example, the pulse wave analyzing apparatus 100 may generate the pulse wave waveform by detecting a change of the skin of the subject due to contraction or expansion of the heart. In addition, for example, the pulse wave analyzing apparatus 100 may generate the pulse wave waveform by detecting the blood vessel or the movement of the blood of the subject due to contraction or expansion of the heart.

In addition, the pulse wave analyzing apparatus 100 similarly generates the pulse wave waveforms of each of the parts based on the extracted images of each of the parts. Accordingly, the pulse wave analyzing apparatus 100 is a determination target whether or not the noise is included, and can generate the pulse wave waveform of the face of the subject, which is the pulse wave waveform to be analyzed. In addition, the pulse wave analyzing apparatus 100 can generate the pulse wave waveforms on the face of the subject, on the left side of the face, and on the right side of the face, which have the pulse wave waveform used when calculating the index value. Here, the description of FIG. 9 will be made.

<One Example of Determining Partial Waveform to be Determined>

Figure 9:
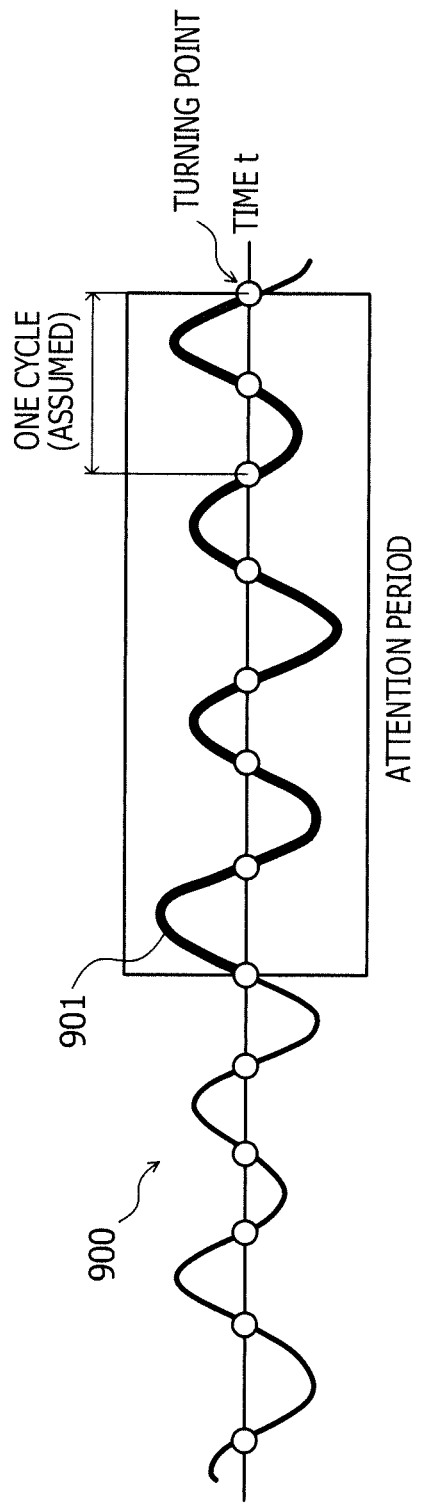
FIG. 9 is an explanatory view illustrating an example of determining a partial waveform of a determination target.

FIG. 9 is an explanatory view illustrating an example of determining the partial waveform of the determination target. In FIG. 9, the pulse wave analyzing apparatus 100 specifies a turning point at which the waveform changes from positive to negative or from negative to positive in a generated pulse wave waveform 900 at any part of the subject. Either part is, for example, a part at which the pulse wave waveform which is a determination target and a calculation source of the index value is generated, specifically, the face of the subject. Either part may be, for example, a part at which the pulse wave waveform which is not a determination target is generated, specifically, may be the left side of the face or the right side of the face.

Next, the pulse wave analyzing apparatus 100 sets a period that corresponds to a predetermined number of cycles as an attention period, assuming that the length of three turning points is one cycle. The predetermined number of cycles may not be an integral multiple periods. The predetermined number of cycles is, for example, 3.5 cycles. The predetermined number of cycles may be, for example, four cycles or the like. The pulse wave analyzing apparatus 100 may set a plurality of attention periods by setting the attention period for each period having the length that corresponds to the predetermined number of cycles.

In addition, the pulse wave analyzing apparatus 100 divides a partial waveform 901 within the attention period in the generated pulse wave waveform 900 at any part of the subject into the partial waveform 901 of the determination target for determining whether or not the noise is included. In addition, in a case where a plurality of attention periods are set, the attention periods may partially overlap each other. Here, the description of FIG. 10 will be made.

<One Example of Calculating First Matching Degree>

Figure 10:
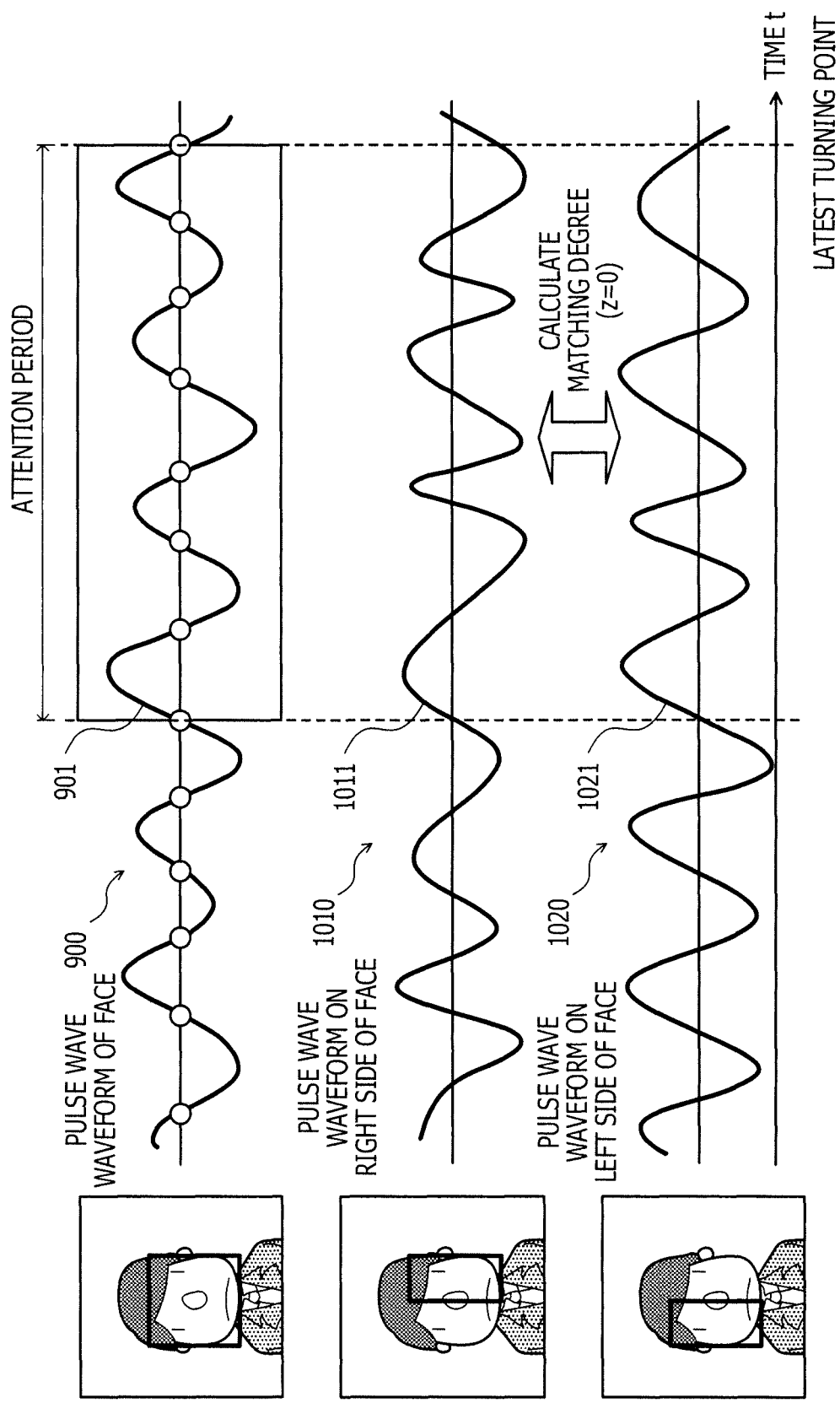
FIG. 10 is an explanatory view illustrating a first example of calculating a first matching degree.

FIG. 10 is an explanatory view illustrating a first example of calculating the first matching degree. Here, the pulse wave analyzing apparatus 100 uses the first matching degree indicating the matching degree between the pulse wave waveforms of the pulse wave waveforms of each of the parts that correspond to the change in volume of the blood that flows through the blood vessel at each of the parts of the subject, as the index value.

When there is no the body movement of the subject, the pulse wave waveforms of each of the parts tend to become a waveform that corresponds to the blood flow similarly flowing from the heart due to expansion and contraction of the heart, and thus, the matching degree tends to increase. Therefore, the first matching degree indicates that the body movement of the subject increases as the value decreases and the pulse wave waveform is in a state of being likely to be disturbed by the noise caused by the body movement of the subject, and indicates the likelihood of the pulse wave is small.

In FIG. 10, the pulse wave analyzing apparatus 100 calculates the first matching degree indicating the matching degree between the partial waveforms within the attention period of the pulse wave waveforms of each of the parts. For example, the pulse wave analyzing apparatus 100 extracts a partial waveform 1011 within the attention period in a pulse wave waveform 1010 on the right side of the face. In addition, the pulse wave analyzing apparatus 100 acquires the data string x(i) of the extracted partial waveform 1011. x(i) is a data string in which the values x(1), . . . , x(X) of the partial waveform 1011 within the attention period are arranged in the order of time. For example, the unit of i is millisecond.

Further, the pulse wave analyzing apparatus 100 extracts a partial waveform 1021 within another period in which the attention period of the pulse wave waveform on the left side of the face is shifted by a shift width z. In addition, the pulse wave analyzing apparatus 100 acquires the data string y(z, i) of the extracted partial waveform 1021. y(z, i) is a data string in which the values y(z, 1), . . . , x(z, X) of the partial waveform 1021 within other periods shifted by the shift width z from the attention period are arranged in the order of time. For z=0, y(z, i) is the partial waveform values y(z, 1), . . . , y(z, X) within the attention period. For example, the unit of z is millisecond.

In addition, the pulse wave analyzing apparatus 100 sets z=0 and substitutes the data string x(i) and the data string y(z, i) into the following equation (1). Accordingly, the pulse wave analyzing apparatus 100 calculates a correlation coefficient s(z) in the following equation (1) as the first matching degree indicating the matching degree between the partial waveform 1011 within the attention period on the right side of the face and the partial waveform 1021 within the attention period on the left side of the face.

[Equation 1]

$$s(z) = \frac{\sum_{i=1}^{x}(x(i)-\bar{x})(y(z,i)-\overline{y(z)})}{\sqrt{\sum_{i=1}^{x}(x(i)-\bar{x})^2}\sqrt{\sum_{i=1}^{x}(y(z,i)-\overline{y(z)})^2}} \quad (1)$$

$\bar{x}$ is an average of x(1), . . . , x(X). $\overline{y(z)}$ is an average of y(z, 1), . . . , y(z, X).

Here, a case where the pulse wave analyzing apparatus 100 calculates the first matching degree indicating the matching degree between the partial waveform 1011 within the attention period on the right side of the face and the partial waveform 1021 within the attention period on the left side of the face by using the above-described equation (1) has been described, but the present embodiment is not limited thereto. For example, the pulse wave analyzing apparatus 100 may calculate the correlation coefficient s(z) of the following equation (2) as the first matching degree by substituting the data string x(i) and the data string y(z, i) into the following equation (2).

[Equation 2]

$$S(z) = \frac{\sum_{i=1}^{x}(x(i)-\bar{x})(y(z,i)-\overline{y(z)})}{\max\left(\sum_{i=1}^{x}(x(i)-\bar{x})^2, \sum_{i=1}^{x}(y(z,i)-\overline{y(z)})^2\right)} \quad (2)$$

Further, for example, the pulse wave analyzing apparatus 100 may calculate the first matching degree indicating the matching degree between the partial waveform 1011 within the attention period on the right side of the face and the partial waveform 1021 within the attention period on the left side of the face by using a Euclidean distance or the normalized Euclidean distance.

In addition, here, a case where the pulse wave analyzing apparatus 100 calculates the first matching degree based on the pulse wave waveforms of each of the parts of the two parts has been described, but the present embodiment is not limited thereto. For example, the pulse wave analyzing apparatus 100 may calculate the first matching degree based on three or more pulse wave waveforms.

Specifically, in a case where there are pulse wave waveforms of each of the parts of the forehead, the left cheek, and the right cheek, the pulse wave analyzing apparatus 100 may acquire the data string indicating the partial waveform within the attention period of each of the parts. In addition, the pulse wave analyzing apparatus 100 may calculate the first matching degree for the combination of each of the data strings by substituting the combination of each of the data strings into the above-described equation (1), and may calculate the average value of the calculated first matching degrees. Accordingly, the pulse wave analyzing apparatus 100 can improve the likelihood of the index value of the first matching degree in a case where each of the parts is not on the same plane.

Specifically, the pulse wave analyzing apparatus 100 may calculate the first matching degree for each of the corresponding combinations, such as a combination of the left cheek and the right cheek or a combination of the upper part of the face and the lower part of the face in a case where there are pulse wave waveforms of each of the parts, such as the left cheek, the right cheek, the upper part of the face, and the lower part of the face. In addition, the pulse wave analyzing apparatus 100 calculates the calculated statistical value of the first matching degree, for example, the minimum value. The statistical values are, for example, an average value, a median value, a maximum value, and a minimum value. Accordingly, the pulse wave analyzing apparatus 100 can calculate the first matching degree that can correspond to various body movements of the subject, and can improve the likelihood of the index value of the first matching degree. Here, the description of FIG. 11 will be made.

Figure 11:
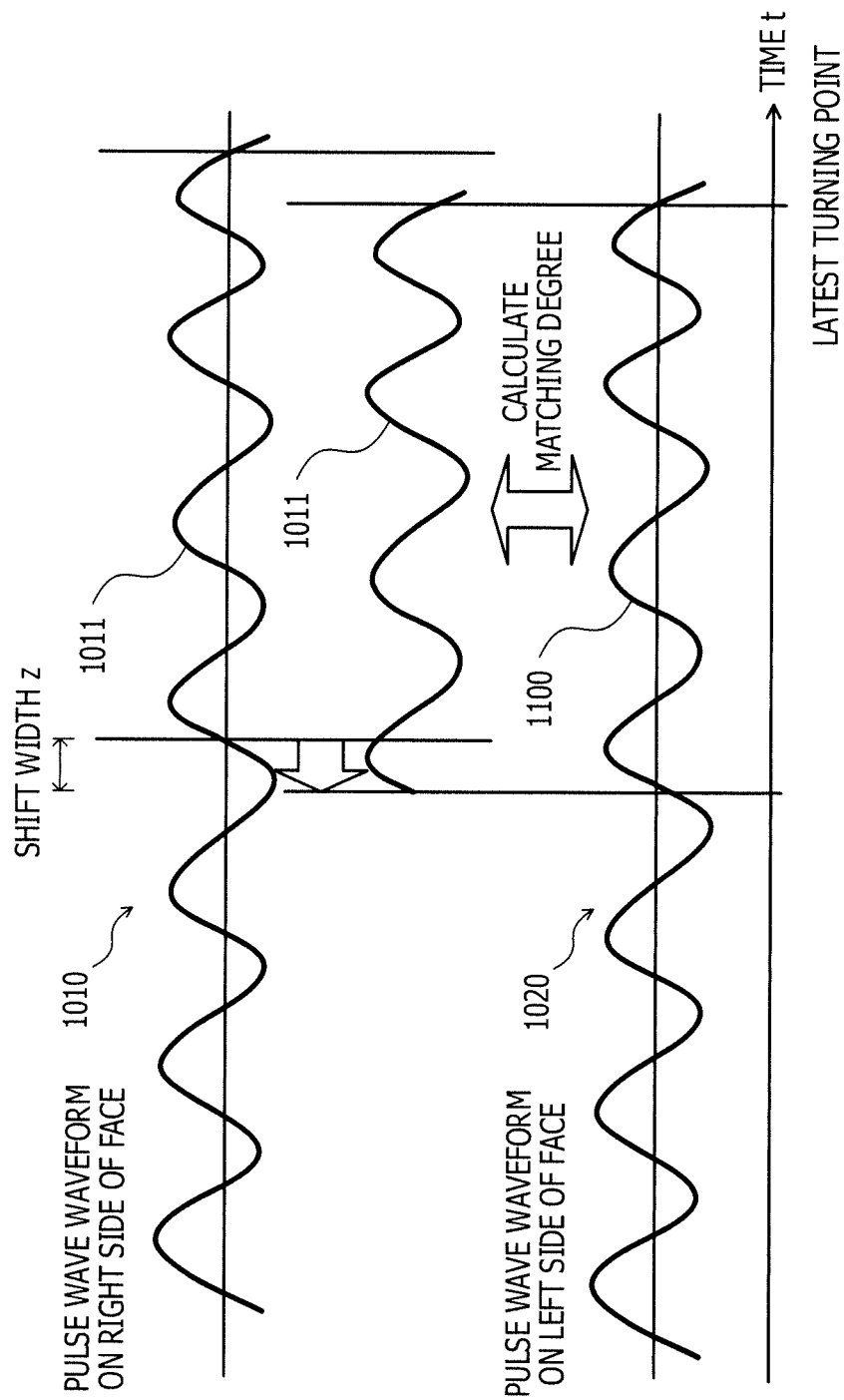
FIG. 11 is an explanatory view illustrating a second example of calculating the first matching degree.

FIG. 11 is an explanatory view illustrating a second example of calculating the first matching degree. Here, in a case where each of the parts of the subject are physically separated from each other, since the distance from the heart is different, the pulse wave waveforms of each of the parts have similar waveforms, but there is a case where the waveforms are shifted in a time direction. Here, when calculating the first matching degree, the pulse wave analyzing apparatus 100 may calculate the first matching degree between the pulse wave waveforms at any part of the subject and the pulse wave waveform at another part.

In FIG. 11, the pulse wave analyzing apparatus 100 calculates the first matching degree between the partial waveform within the attention period of the pulse wave waveforms at any part of the subject and the partial waveform within another period shifted from the attention period by the shift width z in the pulse wave waveform at another part. For example, the unit of z is millisecond.

The pulse wave analyzing apparatus 100 extracts the partial waveform 1011 within the attention period in the pulse wave waveform 1010 on the right side of the face, and acquires the data string $x(i)$ of the extracted partial waveform 1011. $x(i)$ is a data string in which the values $x(1), \ldots, x(X)$ of the partial waveform 1011 within the attention period are arranged in the order of time. For example, the unit of i is millisecond.

In addition, while incrementing the range of $z=-100$ to 100 by 1, the pulse wave analyzing apparatus 100, for example, extracts a partial waveform 1100 within another period shifted from the attention period in a pulse wave waveform 1020 on the left side of the face by the shift width z. In addition, the pulse wave analyzing apparatus 100 acquires the data string $y(z, i)$ of the extracted partial waveform 1100. $y(z, i)$ is a data string in which the values $y(z, 1), \ldots, x(z, X)$ of the partial waveform 1100 within other periods shifted by the shift width z from the attention period are arranged in the order of time. For example, the unit of z is millisecond.

In addition, for example, while incrementing the interval of $z=-100$ to 100 one by one, the pulse wave analyzing apparatus 100 calculates the correlation coefficient $s(z)$ by substituting the data string $x(i)$ and the data string $y(z, i)$ in the above-described equation (1) or the equation (2). Further, the pulse wave analyzing apparatus 100 sets the maximum value among the correlation coefficients $s(z)$ of $z=-100$ to 100 as the first matching degree.

Here, a case where the pulse wave analyzing apparatus 100 calculates the first matching degree by using the above-described equation (1) or the equation (2) has been described, but the present embodiment is not limited thereto. For example, the pulse wave analyzing apparatus 100 may calculate the first matching degree by using the Euclidean distance or the normalized Euclidean distance.

In addition, here, a case where the pulse wave analyzing apparatus 100 calculates the first matching degree based on the pulse wave waveforms of each of the parts of the two parts has been described, but the present embodiment is not limited thereto. For example, the pulse wave analyzing apparatus 100 may calculate the first matching degree based on three or more pulse wave waveforms.

Specifically, in a case where there are pulse wave waveforms of each of the parts of the forehead, the left cheek, and the right cheek, the pulse wave analyzing apparatus 100 calculates the first matching degree between the partial waveform within the attention period and the partial waveform within another period shifted from the attention period by the shift width z for each of the combinations of the parts. In addition, the pulse wave analyzing apparatus 100 may calculate the calculated average value of the first matching degree. Accordingly, the pulse wave analyzing apparatus 100 can improve the likelihood of the index value of the first matching degree in a case where each of the parts is not on the same plane.

Specifically, the pulse wave analyzing apparatus 100 may calculate the first matching degree for each of the corresponding combinations, such as a combination of the left cheek and the right cheek or a combination of the upper part of the face and the lower part of the face in a case where there are pulse wave waveforms of each of the parts, such as the left cheek, the right cheek, the upper part of the face, and the lower part of the face. In addition, the pulse wave analyzing apparatus 100 calculates the calculated minimum value of the first matching degree. Accordingly, the pulse wave analyzing apparatus 100 can calculate the first matching degree that can correspond to various body movements of the subject. Here, the description of FIG. 12 will be made.

<One Example of Calculating Second Matching Degree>

Figure 12:
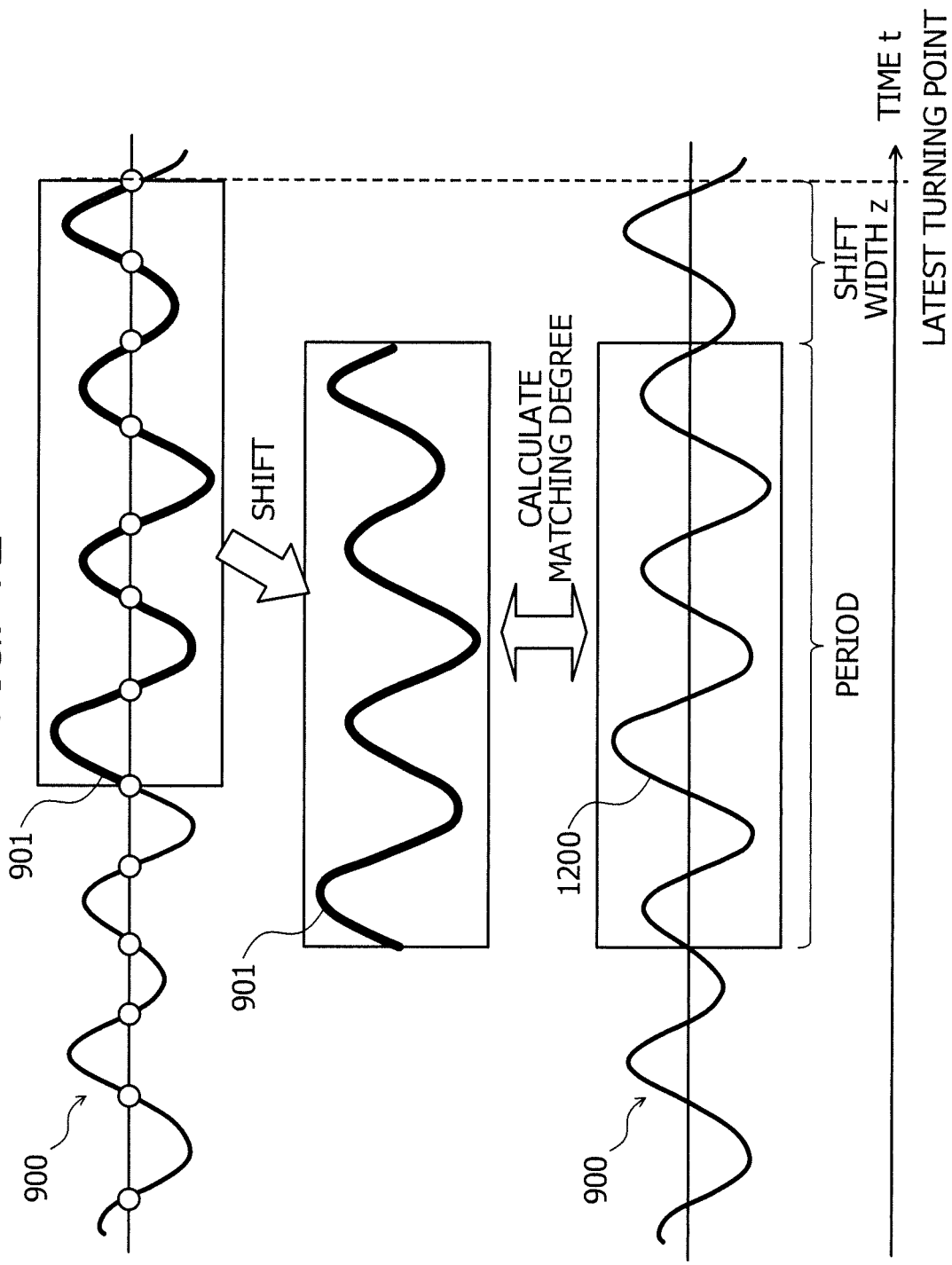
FIG. 12 is an explanatory view illustrating an example of calculating the second matching degree.

FIG. 12 is an explanatory view illustrating an example of calculating the second matching degree. As a technology for calculating the second matching degree, for example, the technology described in Japanese Laid-open Patent Publication No. 2014-176584 can be referred to.

In FIG. 12, the pulse wave analyzing apparatus 100 calculates the second matching degree between the partial waveform within the attention period and the partial waveform within another period shifted from the attention period by the shift width z in the pulse wave waveforms at any part of the subject. For example, the unit of z is millisecond.

For example, the pulse wave analyzing apparatus 100 extracts the partial waveform 901 within the attention period in the pulse wave waveform 900 of the face. In addition, the pulse wave analyzing apparatus 100 acquires the data string x(i) of the extracted partial waveform 901. x(i) is a data string in which the values x(1), ..., x(X) of the partial waveform 901 within the attention period are arranged in the order of time. For example, the unit of i is millisecond.

In addition, while incrementing the range of z=400 to 1500 by 1, the pulse wave analyzing apparatus 100 extracts a partial waveform 1200 within another period shifted from the attention period in the pulse wave waveform 900 of the face by the shift width z. In addition, the pulse wave analyzing apparatus 100 acquires the data string y(z, i) of the extracted partial waveform 1200. y(z, i) is a data string in which the values y(z, 1), ..., x(z, X) of the partial waveform 1200 within other periods shifted by the shift width z from the attention period are arranged in the order of time. For example, the unit of z is millisecond.

Next, while incrementing the interval of z=−400 to 1500 one by one, the pulse wave analyzing apparatus 100 calculates the correlation coefficient s(z) by substituting the data string x(i) and the data string y(z, i) in the above-described equation (1) or the equation (2). Further, the pulse wave analyzing apparatus 100 sets the maximum value among the correlation coefficients s(z) of z=400 to 1500 as the second matching degree. In addition, the pulse wave analyzing apparatus 100 may adopt z when the correlation coefficient s(z) becomes the maximum among z=400 to 1500 as the pulse wave interval.

Here, a case where the pulse wave analyzing apparatus 100 calculates the second matching degree by using the above-described equation (1) or the equation (2) has been described, but the present embodiment is not limited thereto. For example, the pulse wave analyzing apparatus 100 may calculate the second matching degree by using the Euclidean distance or the normalized Euclidean distance. In addition, the second matching degree may be calculated from an index representing the variation of the pulse wave interval. The index representing the pulse wave interval is, for example, the standard deviation of the pulse wave interval or the peak width of the spectral distribution obtained from the wave shape.

<One Example of Determining Whether or not Noise is Included>

Figure 13:
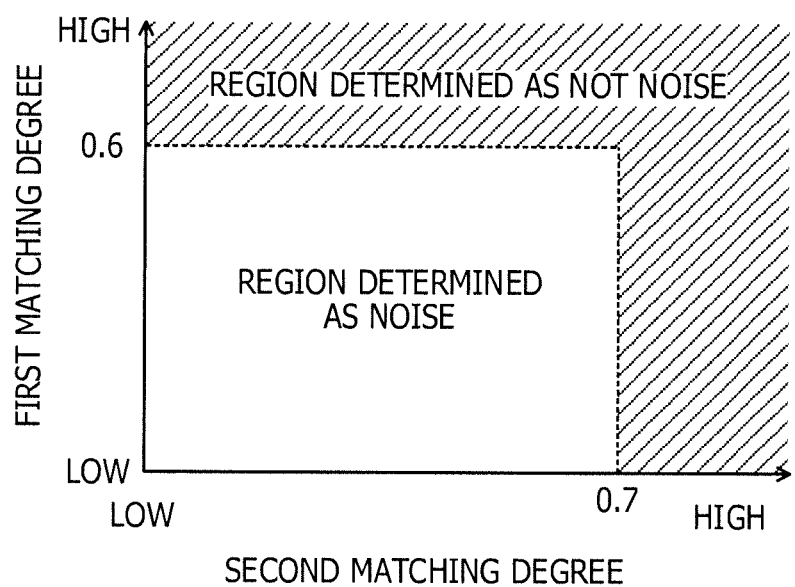
FIG. 13 is an explanatory diagram illustrating an example of determining whether or not noise is included.

FIG. 13 is an explanatory diagram illustrating an example of determining whether or not the noise is included. Here, the first matching degree tends to be a small value because there is a temporal change in irradiation light amount to each of the parts when there is a body movement of a person. In other words, the first matching degree indicates that the possibility of disturbance of the pulse wave waveform by the noise caused by the body movement of the subject is high as the value decreases.

Meanwhile, in a case where the value is large, the second matching degree indicates that the pulse wave waveform is periodic. In other words, the second matching degree has a tendency that the noise is not included in the pulse wave waveform as the value increases. Accordingly, the pulse wave analyzing apparatus 100 can distinguish whether or not the noise is included in the pulse wave waveform based on the tendency of the first matching degree and the tendency of the second matching degree.

In FIG. 13, in a case where the first matching degree is equal to or greater than the first threshold value, the pulse wave analyzing apparatus 100 determines that the noise is not included in the partial waveform within the attention period of the pulse wave waveforms at any part of the subject. The first threshold value is, for example, 0.6. In addition, in a case where the second matching degree is equal to or greater than the second threshold value, the pulse wave analyzing apparatus 100 determines that the noise is not included in the partial waveform within the attention period of the pulse wave waveforms at any part of the subject. The second threshold value is, for example, 0.7.

In a case where the average value of the first matching degree is calculated, the pulse wave analyzing apparatus 100 may determine whether or not the pulse wave waveform includes the noise by comparing the average value of the first matching degree and the first threshold value to each other. In addition, in a case where the minimum value of the first matching degree is calculated, the pulse wave analyzing apparatus 100 may determine whether or not the pulse wave waveform includes the noise by comparing the minimum value of the first matching degree and the first threshold value to each other.

<One Example of Analyzing Pulse Wave Waveform According to Determination Result>

The pulse wave analyzing apparatus 100 analyzes the pulse wave waveforms at any part of the subject by using the partial waveform determined that the noise in the pulse wave waveforms at any part of the subject is not included. In a case where the partial waveform determined to include no noise and the partial waveform determined to include the noise overlap each other, the pulse wave analyzing apparatus 100 may use a part that does not overlap the partial waveform determined to include the noise in the partial waveform determined to include no noise. Accordingly, the pulse wave analyzing apparatus 100 can analyze the pulse wave waveforms at any part of the subject without using the partial waveform including the noise, and it is possible to improve the analysis accuracy.

For example, the pulse wave analyzing apparatus 100 calculates the pulse rate [bpm] by analyzing the pulse wave waveforms at any part of the subject. Further, the pulse wave analyzing apparatus 100 may analyze the pulse wave waveforms at any part of the subject, differentiate the pulse wave waveforms at any part of the subject twice, calculate an acceleration pulse wave waveform, and calculate a vascular age from the acceleration pulse wave waveform. Further, for example, the pulse wave analyzing apparatus 100 may analyze the pulse wave waveforms at any part of the subject and determine whether or not the subject has an arrhythmia.

Here, a case where the pulse wave analyzing apparatus 100 analyzes the pulse wave waveforms at any part of the subject without using the partial waveform including the noise, has been described, but the embodiment is not limited thereto. For example, the pulse wave analyzing apparatus 100 may analyze the pulse wave waveforms at any part of the subject by using the first matching degree, the second matching degree, and the pulse wave waveforms at any part of the subject.

(One Example of Determination Processing Procedure)

Next, one example of the determination processing procedure executed by the pulse wave analyzing apparatus 100 will be described with reference to FIG. 14.

Figure 14:
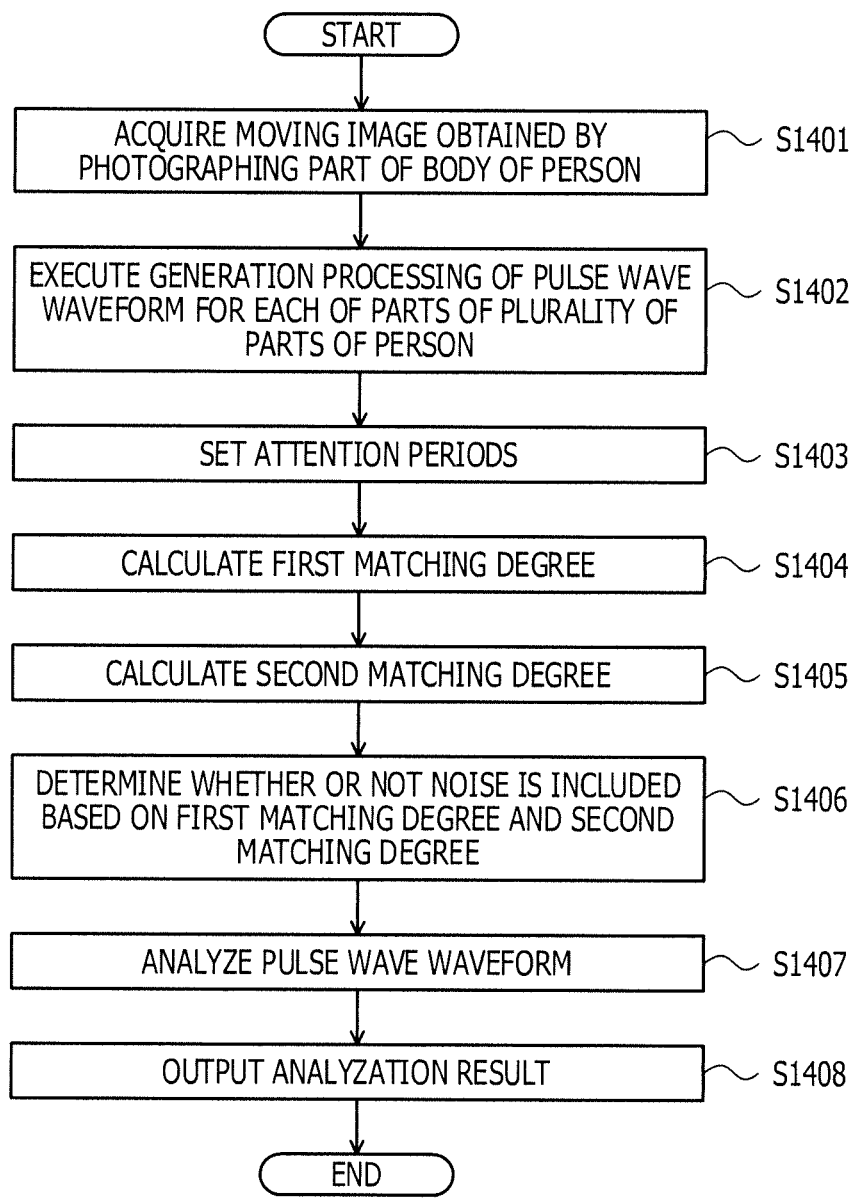
FIG. 14 is a flowchart illustrating an example of a determination processing procedure.

FIG. 14 is a flowchart illustrating an example of a determination processing procedure. In FIG. 14, the pulse wave analyzing apparatus 100 acquires the moving image 101 obtained by photographing a part of the body of a person (step S1401). Next, the pulse wave analyzing apparatus 100 executes generation processing of the pulse wave waveform (to be described later in FIG. 15) for each of the parts of the plurality of parts of a person (step S1402). In addition, the pulse wave analyzing apparatus 100 sets the attention period based on the generated pulse wave waveforms at any part (step S1403).

Next, the pulse wave analyzing apparatus 100 calculates the first matching degree indicating the matching degree between the partial waveforms within the attention period of the generated pulse wave waveforms of each of the parts of the plurality of parts (step S1404). In addition, the pulse wave analyzing apparatus 100 calculates the second matching degree indicating the matching degree between the partial waveform within the attention period and the partial waveform within a period which is a comparison target shifted from the attention period by the shift width in the generated pulse wave waveforms at any part (step S1405).

Next, the pulse wave analyzing apparatus 100 determines whether or not the noise is included in the partial waveform within the attention period in the generated pulse wave waveforms at any part based on the first matching degree and the second matching degree (step S1406). In addition, the pulse wave analyzing apparatus 100 sets the generated pulse wave waveforms at any part based on the determination result (step S1407).

Next, the pulse wave analyzing apparatus 100 outputs the analysis result (step S1408). In addition, the pulse wave analyzing apparatus 100 ends the determination processing. Accordingly, the pulse wave analyzing apparatus 100 determines whether or not the noise is included in the pulse wave waveforms at any part of a person, and to improve the analysis accuracy of the pulse wave waveforms at any part of a person.

(One Example of Generation Processing Procedure)

Next, one example of the generation processing procedure executed by the pulse wave analyzing apparatus 100 will be described with reference to FIG. 15.

Figure 15:
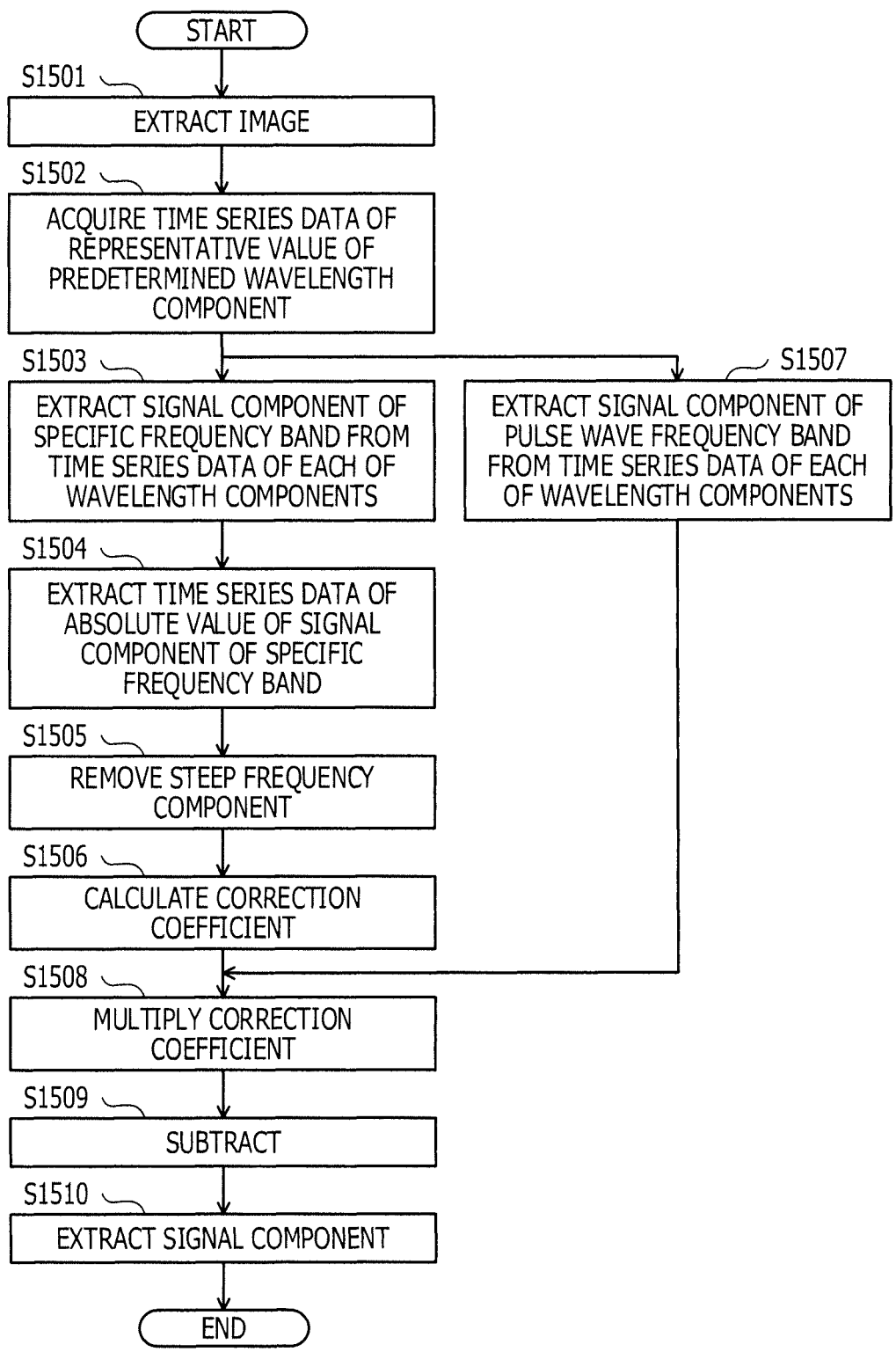
FIG. 15 is a flowchart illustrating an example of a generation processing procedure.

FIG. 15 is a flowchart illustrating an example of the generation processing procedure. In FIG. 15, the pulse wave analyzing apparatus 100 extracts the images of each of the parts of the plurality of parts of persons from the moving image 101 (step S1501).

Next, based on the extracted image, the pulse wave analyzing apparatus 100 acquires the time series data of the representative values of predetermined wavelength components included in the image (step S1502). In addition, the pulse wave analyzing apparatus 100 extracts the signal component in the specific frequency band from the time series data for each of the acquired wavelength components by the BPF (step S1503).

Next, the pulse wave analyzing apparatus 100 extracts the time series data of the absolute value of the signal component in the specific frequency band from the signal component in the specific frequency band for each of the extracted wavelength components (step S1504). In addition, the pulse wave analyzing apparatus 100 performs the smoothing process with respect to the time series data of the absolute value of the specific frequency band for each of the extracted wavelength components by the LPF, and removes steep frequency components (step S1505).

Next, the pulse wave analyzing apparatus 100 calculates a correction coefficient based on the time series data of the absolute value in the specific frequency band for each of the smoothed wavelength components (step S1506). In addition, together with steps S1503 to S1506, the pulse wave analyzing apparatus 100 extracts the signal component in the pulse wave frequency band from the time series data for each of the acquired wavelength components by the BPF (step S1507).

Next, in the pulse wave analyzing apparatus 100, the signal component of any of the extracted pulse wave frequency bands is multiplied by the calculated correction coefficient (step S1508). In addition, in the pulse wave analyzing apparatus 100, the signal component of the pulse wave frequency band of the wavelength component multiplied by a correction coefficient k is subtracted from the signal component of the pulse wave frequency band of any wavelength component (step S1509).

Next, the pulse wave analyzing apparatus 100 extracts the signal component of the pulse wave frequency band of the time series data of the signal after the subtraction by the BPF (step S1510). In addition, the pulse wave analyzing apparatus 100 ends the generation processing. Accordingly, the pulse wave analyzing apparatus 100 can generate the pulse wave waveforms of the subject.

As described above, according to the pulse wave analyzing apparatus 100, it is possible to generate the pulse wave waveforms of each of the parts by analyzing the images of each of the parts of the plurality of parts of the subject extracted from each of the photographed images included in the moving image 101 obtained by photographing the subject. In addition, according to the pulse wave analyzing apparatus 100, it is possible to calculate the first matching degree between the generated pulse wave waveforms of each of the parts and output the calculated first matching degree. Accordingly, the pulse wave analyzing apparatus 100 can improve the analysis accuracy of the pulse wave waveform of the subject by calculating an index value indicating likelihood of pulse waves of the pulse wave waveform of the subject from the moving image 101 of the subject. For example, the pulse wave analyzing apparatus 100 can be used for determination regarding the health of the subject taking into consideration the likelihood of pulse wave of the generated pulse wave waveform.

In addition, according to the pulse wave analyzing apparatus 100, it is possible to generate the pulse wave waveform of the subject by analyzing the image of the subject extracted from each of the photographed images, and to determine whether or not the noise is included in the generated pulse wave waveform of the subject based on the calculated first matching degree. Accordingly, in a case where the calculated first matching degree is relatively small, the pulse wave analyzing apparatus 100 can determine that the noise is included in the generated pulse wave waveforms. In addition, the pulse wave analyzing apparatus 100 may not use the pulse wave waveform including the noise for determination or the like regarding the health of the subject.

In addition, according to the pulse wave analyzing apparatus 100, it is possible to calculate the second matching degree between the partial waveforms of each of the parts of the generated partial waveforms that corresponds to the plurality of predetermined times extracted from the pulse wave waveform of the subject. In addition, according to the pulse wave analyzing apparatus 100, it is possible to determine whether or not the noise is included in the generated pulse wave waveform of the subject based on the calculated first matching degree and the calculated second matching degree. Accordingly, in a case where the calculated first matching degree is relatively small, or in a case where the calculated second matching degree is relatively small, the pulse wave analyzing apparatus 100 can determine that the noise is included in the generated pulse wave waveform. In addition, the pulse wave analyzing apparatus 100 may not use the pulse wave waveform including the noise for determination or the like regarding the health of the subject.

Further, according to the pulse wave analyzing apparatus 100, it is possible to use the photographed images within the predetermined period for each of the photographed images. Accordingly, the pulse wave analyzing apparatus 100 can calculate the index value indicating the likelihood of pulse wave in the pulse wave waveform within the predetermined period of the pulse wave waveform generated from the entire moving image 101. As a result, the pulse wave analyzing apparatus 100 can determine whether or not the noise is included in the pulse wave waveform at predetermined intervals.

Further, according to the pulse wave analyzing apparatus 100, it is possible to use the photographed images within the predetermined period which are different at each of the parts, for each of the photographed images. Accordingly, even in a case where the plurality of parts having different pulse timings are used, the pulse wave analyzing apparatus 100 can take the timing of the pulse for each of the parts into consideration, and calculate the first matching degree of the pulse wave waveform for each of the parts.

Further, according to the pulse wave analyzing apparatus 100, it is possible to use two or more interlocking parts at the plurality of parts. Accordingly, the pulse wave analyzing apparatus 100 can make similar movements appear at each of the plurality of parts according to the body movement of the subject, and make it easier to calculate the index value of likelihood of pulse wave.

Further, according to the pulse wave analyzing apparatus 100, it is possible to use two or more interlocking parts which are not on the same plane at the plurality of parts. Accordingly, the pulse wave analyzing apparatus 100 can make similar movements appear at each of the plurality of parts according to the body movement of the subject, and make it easier to calculate the index value of likelihood of pulse wave.

Further, according to the pulse wave analyzing apparatus 100, it is possible to use symmetrically existing parts on the face of the subject at the plurality of parts. Accordingly, the pulse wave analyzing apparatus 100 can make similar movements appear at each of the plurality of parts according to the body movement of the subject, and make it easier to calculate the index value of likelihood of pulse wave.

In addition, according to the pulse wave analyzing apparatus 100, it is possible to determine whether or not the noise is included in the generated pulse wave waveform of the subject based on the average value of the first matching degrees of the pulse wave waveforms of each of the parts of the three or more parts. Accordingly, the pulse wave analyzing apparatus 100 can make it easier to determine whether or not the noise caused by various body movements of the subject is included in the generated pulse wave waveform of the subject.

Further, according to the pulse wave analyzing apparatus 100, it is possible to calculate the first matching degree between the pulse wave waveforms of each of the parts in the combination for each of the predetermined combinations at the plurality of parts. In addition, the pulse wave analyzing apparatus 100 can determine whether or not the noise is included in the generated pulse wave waveform of the subject, based on the minimum value of the calculated first matching degrees for each of the combinations. Accordingly, the pulse wave analyzing apparatus 100 can make it easier to determine whether or not the noise caused by various body movements of the subject is included in the generated pulse wave waveform of the subject.

In addition, according to the pulse wave analyzing apparatus 100, it is possible to generate the pulse wave waveform of the subject by analyzing the image of the subject extracted from each of the photographed images, and to output the calculated first matching degree and the generated pulse wave waveform of the subject in association with each other. Accordingly, the pulse wave analyzing apparatus 100 can notify the user of the calculated first matching degree as the index value of likelihood of pulse waves for the pulse wave waveform of the subject.

In addition, according to the pulse wave analyzing apparatus 100, based on the calculated first matching degree, it is possible to determine whether or not the noise is included in the pulse wave waveforms at any part of the plurality of parts. Accordingly, in a case where the calculated first matching degree is relatively small, the pulse wave analyzing apparatus 100 can determine that the noise is included in the generated pulse wave waveforms. In addition, the pulse wave analyzing apparatus 100 can may not use the pulse wave waveform including the noise for determination or the like regarding the health of the subject.

In addition, according to the pulse wave analyzing apparatus 100, it is possible to output the calculated first matching degree and the pulse wave waveforms at any part of the plurality of parts in association with each other. Accordingly, the pulse wave analyzing apparatus 100 can notify the user of the calculated first matching degree as the index value of the likelihood of pulse waves for the pulse wave waveforms at any part of the plurality of parts.

In addition, the pulse wave analyzing method described in the embodiment can be realized by executing a prepared program on a computer, such as a personal computer or a workstation. The pulse wave analyzing program is recorded in a recording medium that can be read by the computer, such as a hard disk, a flexible disk, a CD-ROM, an MO, or a DVD, and is executed by being read from the recording medium by the computer. Also, the pulse wave analyzing program may be distributed via a network, such as the Internet.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A pulse wave analysis apparatus comprising:
   a memory; and
   a processor coupled to the memory and the processor configured to execute a process, the process including:
      extracting, from each of a plurality of captured images of a subject, a plurality of image areas corresponding to each of a plurality of parts of the subject respectively, the plurality of parts being not on a same plane and moving together in accordance with the subject's movement, the plurality of parts include three or more parts;

generating pieces of waveform data corresponding to the plurality of parts based on an image analysis for the plurality of image areas, each of the pieces of waveform data indicating a pulse wave of the subject;

calculating a first matching degree between the pieces of waveform data;

calculating a statistical value of a plurality of first matching degrees, the plurality of first matching degrees indicating the matching degree between two or more combinations of two pieces of waveforms data selected from the plurality of waveform data; and determining whether a noise is included in the pieces of waveform data based on the first matching degree.

2. The pulse wave analysis apparatus according to claim 1, wherein
the determining determines that the noise is included in the pieces of waveform data when the first matching degree is lower than a predetermined threshold.

3. The pulse wave analysis apparatus according to claim 1, wherein
the process further comprises:
obtaining, from one of the pieces of waveform data, a plurality of partial waveform data, the plurality of partial waveforms data being generated by dividing the one of the pieces of waveform data at predetermined time intervals;
calculating a second matching degree indicating a matching degree between the plurality of partial waveforms data; and
determining whether the noise is included in the one of the pieces of waveform data based on the first matching degree and the second matching degree.

4. The pulse wave analysis apparatus according to claim 1, wherein
the plurality of waveform data indicates the pulse wave of the subject within a predetermined period.

5. The pulse wave analysis apparatus according to claim 1, wherein
the calculating calculates the first matching degree with shifting at least one of the plurality of waveform data in a time direction.

6. The pulse wave analysis apparatus according to claim 1, wherein
the plurality of parts include two or more parts that move interlocking with each other.

7. The pulse wave analysis apparatus according to claim 1, wherein
the plurality of parts include two or more parts that are not on a same plane.

8. The pulse wave analysis apparatus according to claim 1, wherein
the plurality of parts include two or more parts that exist symmetrically on the body of the subject.

9. The pulse wave analysis apparatus according to claim 1, wherein
the plurality of first matching degrees indicating the matching degree between two pieces of waveforms data selected from the plurality of waveform data in a round-robin.

10. The pulse wave analysis apparatus according to claim 1, wherein the process further comprises:
outputting the calculated first matching degree and the pieces of waveform data in association with each other.

11. The pulse wave analysis apparatus according to claim 1, wherein
the process further comprises:
specifying at least one of the pieces of waveform data including the noise when the noise is included in the pieces of waveform data.

12. The pulse wave analysis apparatus according to claim 1, wherein
the process further comprises:
outputting the calculated first matching degree and one of the pieces of waveform data in association with each other.

13. A pulse wave analysis method executed by a computer, the pulse wave analysis method comprising:
extracting, from each of a plurality of captured images of a subject, a plurality of image areas corresponding to each of a plurality of parts of the subject respectively, the plurality of parts being not on a same plane and moving together in accordance with the subject's movement, the plurality of parts include three or more parts;
generating pieces of waveform data corresponding to the plurality of parts based on an image analysis for the plurality of image areas, each of the pieces of waveform data indicating a pulse wave of the subject;
calculating a first matching degree between the pieces of waveform data;
calculating a statistical value of a plurality of first matching degrees, the plurality of first matching degrees indicating the matching degree between two or more combinations of two pieces of waveforms data selected from the plurality of waveform data; and
determining whether a noise is included in the pieces of waveform data based on the first matching degree.

14. A non-transitory computer-readable storage medium storing a program that causes a computer to execute a process, the process comprising:
extracting, from each of a plurality of captured images of a subject, a plurality of image areas corresponding to each of a plurality of parts of the subject respectively, the plurality of parts being not on a same plane and moving together in accordance with the subject's movement, the plurality of parts include three or more parts;
generating pieces of waveform data corresponding to the plurality of parts based on an image analysis for the plurality of image areas, each of the pieces of waveform data indicating a pulse wave of the subject;
calculating a first matching degree between the pieces of waveform data;
calculating a statistical value of a plurality of first matching degrees, the plurality of first matching degrees indicating the matching degree between two or more combinations of two pieces of waveforms data selected from the plurality of waveform data; and
determining whether a noise is included in the pieces of waveform data based on the first matching degree.

* * * * *